(12) United States Patent
Buchanan

(10) Patent No.: US 7,364,914 B2
(45) Date of Patent: Apr. 29, 2008

(54) METHOD FOR DILUTING A FLUID AND DETECTING ANALYTES WITHIN A DILUTED FLUID

(75) Inventor: Thomas M. Buchanan, Tacoma, WA (US)

(73) Assignee: Clarity Diagnostics, Inc., Summer, WA (US)

( * ) Notice: Subject to any disclaimer, the term of this patent is extended or adjusted under 35 U.S.C. 154(b) by 639 days.

(21) Appl. No.: 10/413,446

(22) Filed: Apr. 11, 2003

(65) Prior Publication Data

US 2004/0002165 A1 Jan. 1, 2004

Related U.S. Application Data

(63) Continuation of application No. PCT/US01/32456, filed on Oct. 18, 2001.

(60) Provisional application No. 60/241,409, filed on Oct. 18, 2000.

(51) Int. Cl.
*G01N 1/10* (2006.01)

(52) U.S. Cl. .................. 436/180; 436/178; 422/58; 422/68.1; 422/101

(58) Field of Classification Search .................. 422/56, 422/58, 101, 68.1; 436/177–178, 174, 180
See application file for complete search history.

(56) References Cited

U.S. PATENT DOCUMENTS

| | | | |
|---|---|---|---|
| 4,797,260 A * | 1/1989 | Parker | 422/101 |
| 4,868,131 A | 9/1989 | Hiratsuka | |
| 5,147,609 A | 9/1992 | Grenner | |
| 5,240,862 A * | 8/1993 | Koenhen et al. | 436/178 |
| 5,260,221 A * | 11/1993 | Ramel et al. | 436/169 |
| 5,266,219 A * | 11/1993 | Pall et al. | 210/767 |
| 5,419,870 A * | 5/1995 | Parker | 422/56 |
| 5,436,129 A * | 7/1995 | Stapleton | 435/6 |
| 5,589,399 A * | 12/1996 | Allen et al. | 436/169 |
| 5,599,715 A | 2/1997 | Warren, III et al. | |
| 5,607,863 A | 3/1997 | Chandler | |
| 5,652,148 A * | 7/1997 | Doshi et al. | 436/178 |
| 5,698,395 A | 12/1997 | Ritterband et al. | |
| 5,744,098 A * | 4/1998 | Kratzer et al. | 422/73 |
| 5,792,425 A | 8/1998 | Clark et al. | |
| 5,849,249 A * | 12/1998 | Jones et al. | 422/101 |
| 5,879,951 A * | 3/1999 | Sy | 436/514 |
| 5,882,940 A | 3/1999 | Ronn | |
| 5,905,038 A * | 5/1999 | Parton | 435/287.6 |
| 5,916,521 A * | 6/1999 | Bunce et al. | 422/56 |
| 5,972,294 A * | 10/1999 | Smith et al. | 422/58 |
| 6,010,912 A | 1/2000 | Davies | |

(Continued)

*Primary Examiner*—Brian R. Gordon
(74) *Attorney, Agent, or Firm*—Christensen O'Connor Johnson Kindness PLLC

(57) ABSTRACT

The present invention provides a method and device for processing, sampling, and diluting a fluid and for detecting an analyte within the processed, sampled, and diluted fluid. In the method and device for processing, sampling, and diluting a fluid, an amount of fluid to be processed, sampled, and diluted is accepted by a porous membrane; a portion of the membrane saturated with the fluid is isolated thereby defining a predetermined sample volume of fluid; and the predetermined fluid volume sample is then released from the isolated membrane with a specified quantity of a fluid diluent to provide a diluted fluid sample. Analytes within the diluted fluid sample are detected by test strips in fluid contact with the diluted fluid sample.

28 Claims, 17 Drawing Sheets

U.S. PATENT DOCUMENTS

| | | | |
|---|---|---|---|
| 6,013,460 A | 1/2000 | Levin | |
| 6,036,659 A | 3/2000 | Ray et al. | |
| 6,057,165 A | 5/2000 | Mansour | |
| 6,083,760 A | 7/2000 | Ditlow et al. | |
| 6,117,398 A * | 9/2000 | Bienhaus et al. | 422/101 |
| 6,126,900 A | 10/2000 | Hildenbrand | |
| 6,146,902 A * | 11/2000 | McMaster | 436/177 |
| 6,242,261 B1 * | 6/2001 | Schoenau et al. | 436/26 |
| 6,271,045 B1 | 8/2001 | Douglas et al. | |
| 6,284,194 B1 | 9/2001 | Chu | |
| 6,352,862 B1 * | 3/2002 | Davis et al. | 436/510 |
| 6,358,730 B1 * | 3/2002 | Kane | 435/297.5 |
| 6,489,132 B1 * | 12/2002 | Gordon et al. | 435/7.92 |
| 6,632,399 B1 * | 10/2003 | Kellogg et al. | 422/72 |
| 6,656,741 B1 * | 12/2003 | Nelson et al. | 436/169 |
| 6,756,230 B2 * | 6/2004 | Noda et al. | 436/8 |
| 6,863,866 B2 * | 3/2005 | Kelly et al. | 422/56 |
| 6,913,152 B2 * | 7/2005 | Zuk, Jr. | 210/406 |
| 7,037,425 B2 * | 5/2006 | Lee et al. | 210/321.75 |
| 2003/0049857 A1 * | 3/2003 | Chan | 436/170 |
| 2006/0234210 A1 * | 10/2006 | Kenan et al. | 435/5 |

* cited by examiner

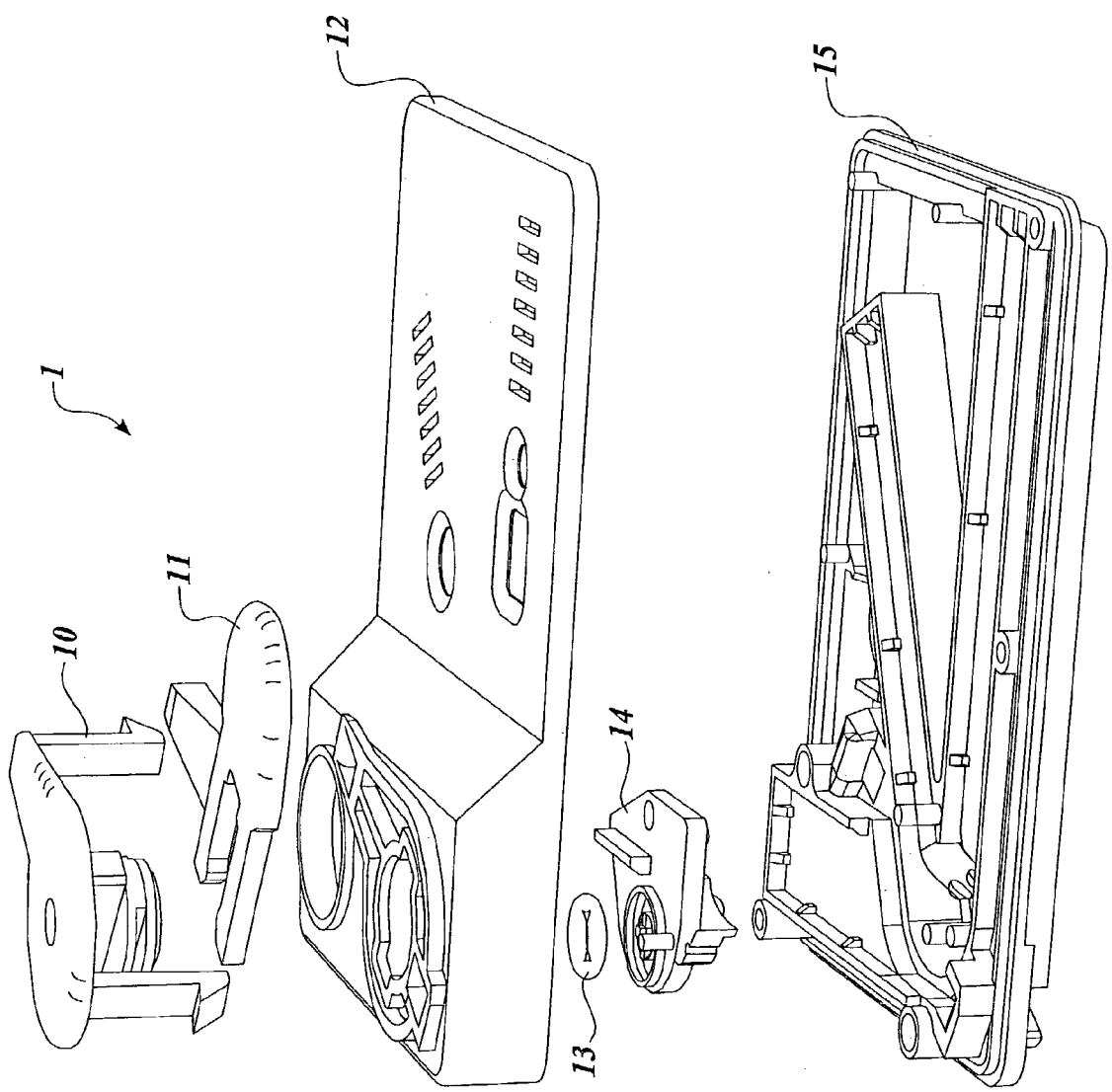

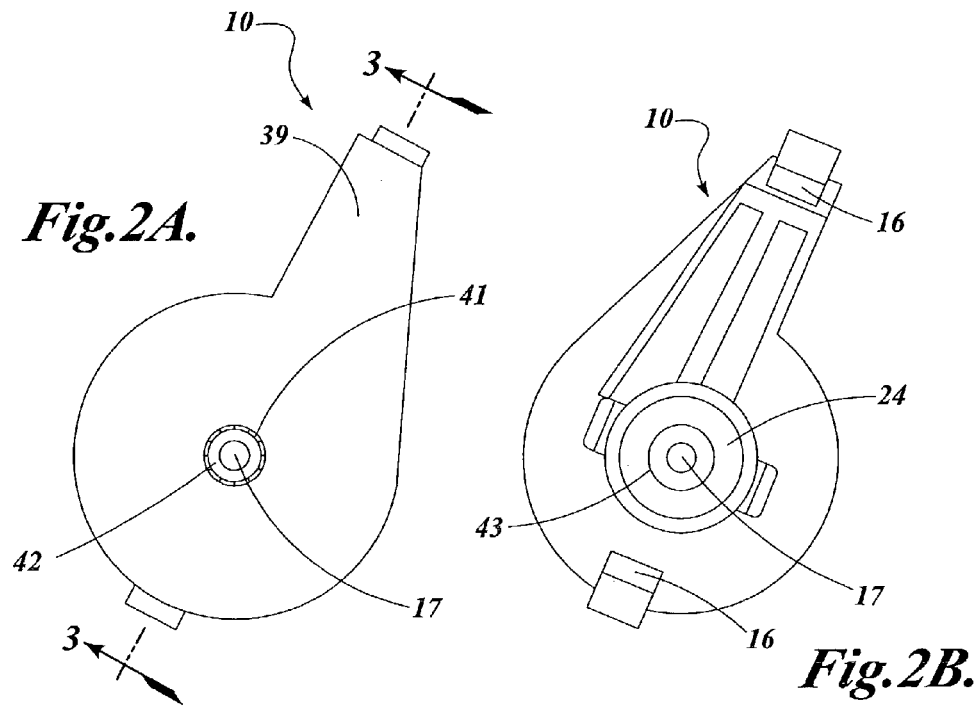
*Fig.2A.*
*Fig.2B.*
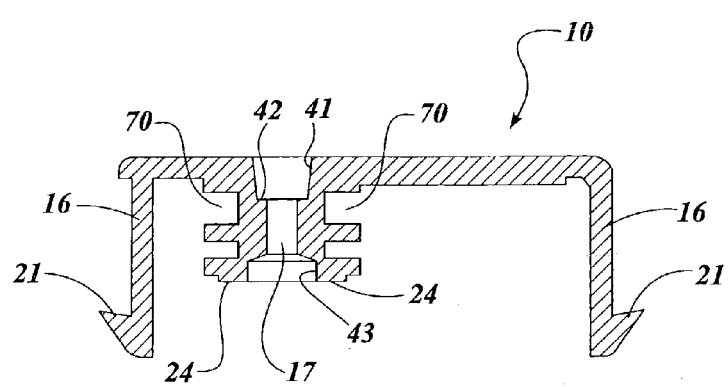
*Fig.3.*

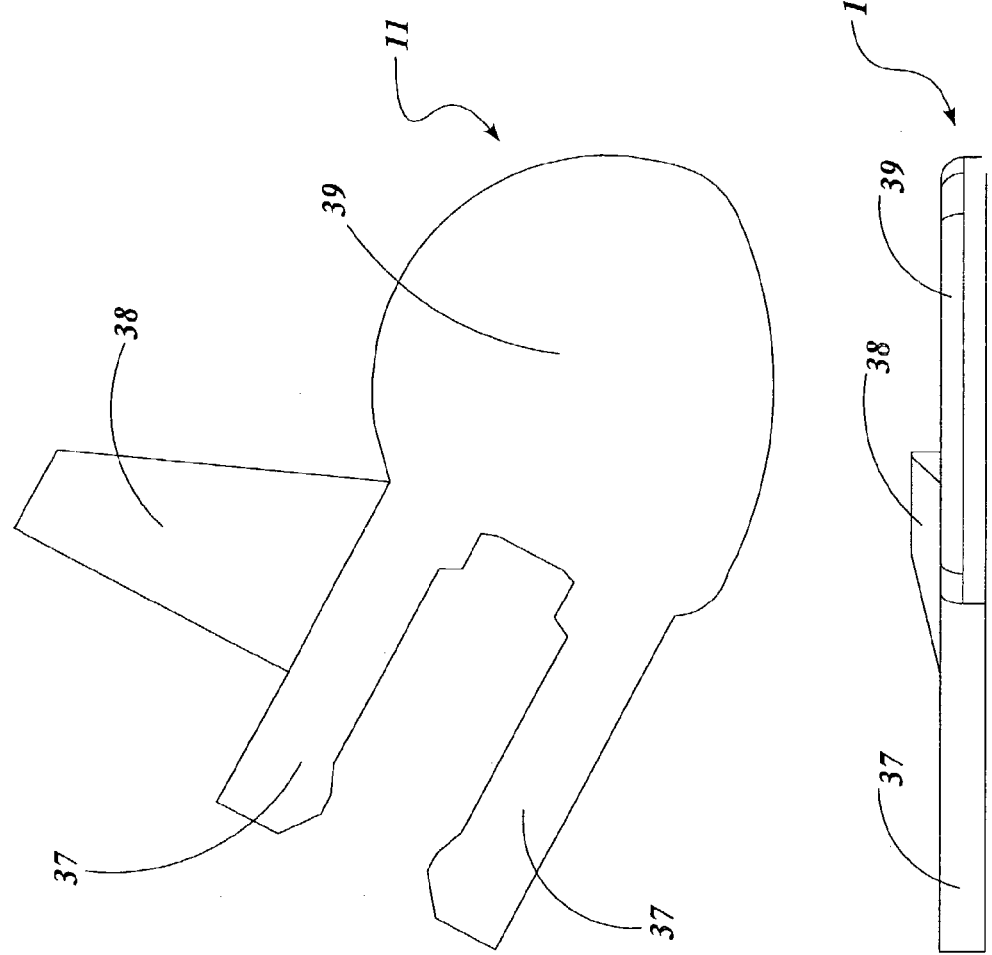

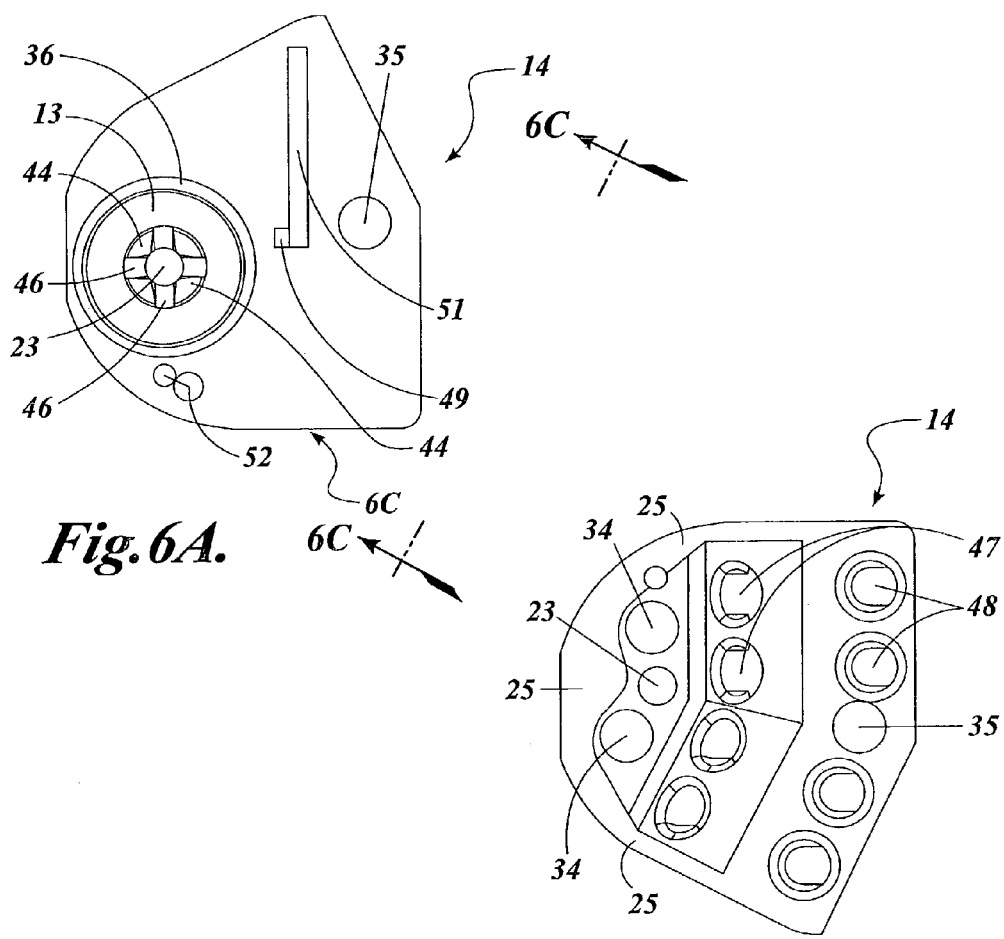
Fig.6A.
Fig.6B.
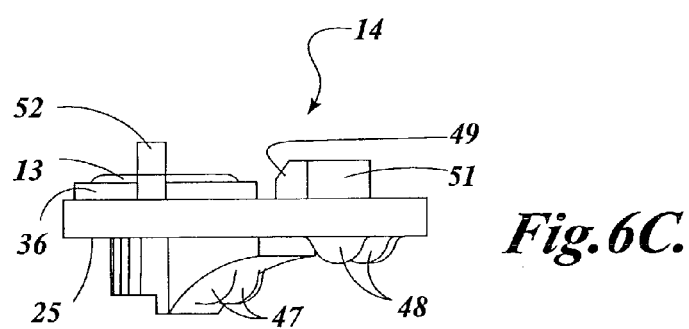
Fig.6C.

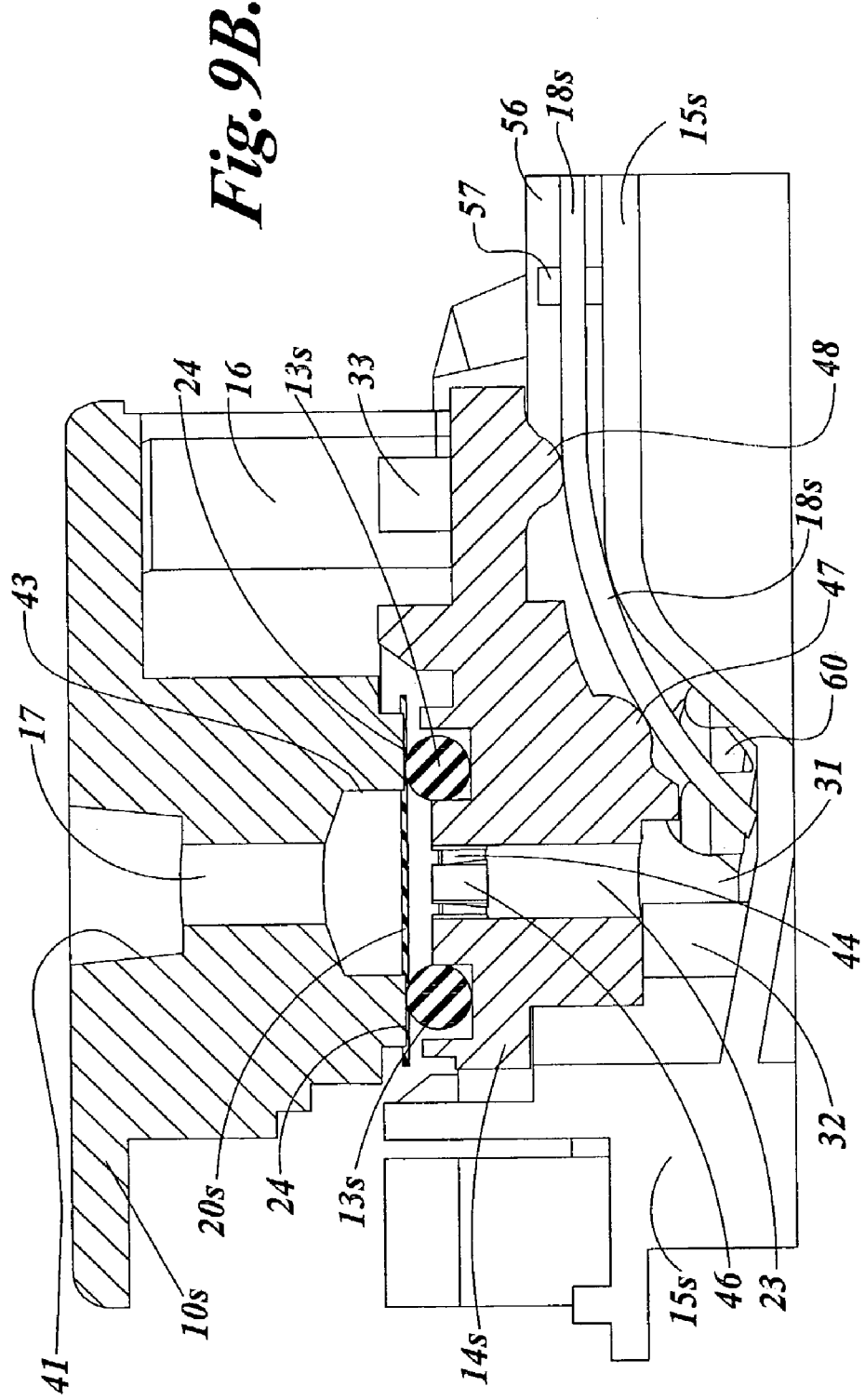

SEQUENCE LISTING

```
<160> NUMBER OF SEQ ID NOS: 1
<210> SEQ ID NO 1
<211> LENGTH: 35
<212> TYPE: PRT
<213> ORGANISM: homo sapien

<400> SEQUENCE: 1

Arg Ile Leu Ala Val Glu Arg Tyr Leu Lys Asp Gln Gln Leu Leu Gly
1               5                   10                  15

Ile Trp Gly Cys Ser Gly Lys Leu Ile Cys Thr Thr Ala Val Pro Trp
            20                  25                  30

Asn Ala Ser
        35
```

US 7,364,914 B2

METHOD FOR DILUTING A FLUID AND DETECTING ANALYTES WITHIN A DILUTED FLUID

CROSS-REFERENCES TO RELATED APPLICATIONS

This application is a continuation of pending International Application No. PCT/US01/32456 designating the United States, filed Oct. 18, 2001, which claims the benefit of U.S. Provisional Patent Application No. 60/241,409, filed Oct. 18, 2000. Each application is incorporated herein by reference in its entirety.

FIELD OF THE INVENTION

The present invention relates to a method and device for processing, sampling, and diluting a fluid and to a method and device for detecting analytes within a processed, sampled, and diluted fluid.

BACKGROUND OF THE INVENTION

Within countries of the world with sophisticated and well-developed medical care systems and facilities, there remain substantial portions of the population that do not access the medical care system. Those who fail to obtain medical diagnoses may represent up to 50% of those at risk for some medical conditions. This failure to access medical diagnosis and care may be due to fear, mistrust, restricted availability, or lack of information or finances. Undiagnosed and untreated individuals serve as a reservoir for increased spread of infection. In the past year, new AIDS cases in San Francisco have doubled to 900 (Investors Business Daily, page A2, Jul. 3, 2000) marking what many doctors fear is a breakdown of our current approach to controlling the infection.

In countries with less developed medical care systems and sophisticated diagnostic testing laboratories, most of the population may not receive prompt diagnosis of potentially treatable conditions. Illnesses such as AIDS, tuberculosis, malaria, and other infectious diseases may drain the country's talent and economic resources to the extreme, with an overall reduction in the standard of living and gross domestic product. (Confronting AIDS, Public Priorities in a Global Epidemic, World Bank Research Report, 1997). In sub-Saharan Africa, more than 10% of the population aged 15-49 carries HIV. In seven of the sixteen countries 20% are infected and in one country, Botswana, one in every three adults carries HIV (Investors Business Daily, page A1, Jun. 28, 2000, Global View of HIV Infection). This toll of medical illness stands as a barrier to becoming part of the community of twenty-first century planet earth with all of its benefits in education, communication and information exchange. These countries risk being hopelessly mired in sickness, death, and economic instability, without the help of more developed countries and new methods of diagnosis, treatment and prevention of disease.

Inexpensive, widely available and easily performed diagnostic tests that could be used by individuals anywhere and at any time, without the need of instrumentation or formal training, would contribute to earlier diagnosis of medical conditions for which the tests were available. These tests would also facilitate improved education regarding those medical conditions being detected by empowering individuals to become involved in their early detection and treatment. Earlier detection and improved education would be expected to result in reduced transmission of those infections for which tests were available to individuals, with the result of benefiting the entire society in terms of fewer infections, and increased health and workforce productivity. Researchers at the Centers for Disease Control in Atlanta, Ga., have used mathematical models to predict that availability of rapid tests for HIV would lead to testing of at least an additional 700,000 people, and detect more than 8,000 additional infected individuals (Los Angeles Times, page A10, Jun. 14, 2000, FDA Blamed for Holding Up Rapid AIDS Tests).

The major technological impediment to development of diagnostic tests suitable for use by individuals has been the lack of device formats that are both accurate and user-friendly for individuals. Accurate test methods have been available for many years but most have required instrumentation. A test that requires instrumentation does not fulfill the needs of individuals who do not choose to or cannot access the medical system, and hence do not become tested. A user-friendly test must be capable of being quickly performed by individuals who have no formal training, and it should require few steps and allow testing in any location at anytime chosen by the user.

In recent years, user-friendly diagnostic tests have been developed that allow individuals to detect analytes in undiluted fluid samples. Examples are pregnancy tests that individuals may purchase in any large supermarket and perform on undiluted urine at any location and at any time that they choose. Patents by Ullman et al., U.S. Pat. No. 4,857,453, issued Aug. 15, 1989; Nazareth et al., U.S. Pat. No. 5,739,041, issued Apr. 14, 1998, and Pawlak et al., U.S. Pat. No. 5,770,460 issued Jun. 23, 1998, are examples of urine HCG tests for pregnancy. Widely available tests for detecting serum glucose may be easily performed .by individuals, but they still require instrumentation. Tests requiring instrumentation are more expensive and do not fit our strict definition of being user-friendly.

Some analytes may be detected in undiluted whole blood, serum or plasma. U.S. Pat. No. 5,762,871, by Neyer, issued Mar. 10, 1998, and U.S. Pat. No. 6,027,692 by Galen et al., issued Feb. 22, 2000, teach tests of undiluted blood serum or plasma for glucose and fructosamine. U.S. Pat. No. 5,166,051 by Killeen et al., issued Nov. 24, 1992, instructs regarding tests of whole blood for analyzing serum cholesterol.

For other tests and assay formulations, detection is more accurate only after dilution of the test liquid. An example is the test for antibodies to HIV. Commercially available immunoassays, as well as rapid strip format tests for HIV antibody, routinely dilute the sample approximately 1:100 before testing, as shown in U.S. Pat. No. 5,922,533 by Vallari et al., issued Jul. 13, 1999. In these tests a uniform dilution. of serum is prepared in a separate location, and the test is then conducted with the uniformly diluted serum.

Attempts to dilute plasma or serum within the test device have employed washing the plasma or serum from a plasma separator/collector pad. An example is that taught by Bernstein et al., U.S. Pat. No. 5,753,497. The resulting dilutions are variable depending upon the volumes of wash fluid added. In addition, the dilutions are not uniform and result in gradient concentrations of serum components migrating down the test strip. The initial eluents from the collector pad contain high concentrations of plasma or serum relative to diluent, and later eluents contain small amounts since most of the plasma or serum has already been washed from the collector pad. This may produce undesirable effects on test performance, such as inconsistent migration rates down the test strip, or inadequate completion of reactivity between test labeling reagents and plasma or serum components that are present in high concentrations, such as immunoglobulin. This results in variations in the time required to complete the test and in some instances adverse effects on sensitivity or specificity.

Individuals conducting a test at home, or staff in a physician's office or point of care location, cannot easily separate plasma or serum from whole blood. They also cannot safely use pipettes to produce a reliable dilution for testing. Persons conducting the test also will not usually have available to them instrumentation for evaluating test strip results.

It would be useful to have a method and device that permits individuals to separate plasma or serum from fingerstick whole blood and obtain a reliable and relatively uniform dilution of that serum or plasma for testing. It would further be useful for the device design to allow migration of the diluted liquid sample along diagnostic test strips contained within the device, so that a diagnostic test result is rapidly produced. Optimally, the test device must provide a clear result that is easily interpreted by visual observation without instrumentation. Finally, to be widely accepted for testing anywhere and at anytime, the device and method must provide these results with a minimum number of easily performed steps and provide the diagnostic test result within approximately ten minutes.

A method and device that would permit reliable dilution of a sample liquid, and rapid determination of the presence or absence of specific analytes within that diluted sample, without requirements of formal training or instruments, would be very useful worldwide. The method and device of this invention seek to fulfill this need.

SUMMARY OF THE INVENTION

The present invention relates to a method and device for processing, sampling, and diluting a fluid and to a method and device for detecting analytes within the processed, sampled, and diluted fluid.

In one aspect, the invention provides a method for processing and sampling a fluid. In the method, at least a portion of a porous membrane is saturated with a first fluid. A portion of the membrane saturated with the first fluid is then isolated and a second fluid is applied to the isolated portion of the membrane releasing the first fluid from the isolated portion of the membrane. The first fluid can be biological fluid such as whole blood or urine. In one embodiment, the first fluid is applied to the membrane at position other than at the isolated portion of the membrane and is migrated to the isolated portion of the membrane. Depending on the application, the second fluid can be a gas or a liquid.

In another aspect of the invention, a method for diluting a liquid sample is provided. In the method, at least a portion of a porous membrane is saturated with a processed liquid. The portion of the membrane saturated with the processed liquid is isolated and a diluent is applied to the isolated portion releasing the liquid sample from the isolated portion of the membrane to provide a diluted liquid sample. The liquid sample can be biological fluid such as whole blood or urine. In one embodiment, the first fluid is applied to the membrane at position other than at the isolated portion of the membrane and is migrated to the isolated portion of the membrane.

In a further aspect, the invention provides a method for detecting an analyte in a liquid sample. In the method, at least a portion of a porous membrane is saturated with a liquid sample containing an analyte. A portion of the membrane saturated with the liquid sample is then isolated and a diluent is applied to the isolated portion releasing the liquid sample from the isolated portion of the membrane. The released and diluted liquid is then directed to receptacle in fluid communication with a test strip where the presence of the analyte is detected. In one embodiment, the receptacle can be in fluid communication with a second strip, for example, a control strip. In one embodiment, the method detects an antibody to HIV. In another embodiment, the method detects an antibody to H. pylori antigen. In a further embodiment, the method detects HCG antigen.

In another aspect of the invention, a device for processing and sampling a fluid is provided. In one embodiment, the device includes a membrane for receiving a first fluid; first and second members adjacent opposing major surfaces of the membrane for isolating a portion of the membrane, and a receptacle in fluid communication with the isolated membrane for receiving fluid from the isolated membrane. The first and second members can be engaged with the membrane to isolate a portion of the membrane. The isolated portion of the membrane maintains a void volume substantially the same as the void volume of the unengaged membrane.

In another aspect, the invention provides a device for diluting a liquid sample. In one embodiment, the device includes a membrane for receiving a liquid, first and second members adjacent opposing major surfaces of the membrane for isolating a portion of the membrane, and a receptacle in fluid communication with the isolated membrane for receiving the sample of liquid from the isolated membrane. The first and second members can be engaged with the membrane to isolate a portion of the membrane. The isolated portion of the membrane maintains a void volume substantially the same as the void volume of the unengaged membrane.

In another aspect of the invention, a device for detecting an analyte in a liquid sample is provided. In one embodiment, the device includes a membrane for receiving a liquid, first and second members adjacent opposing major surfaces of the membrane for isolating a portion of the membrane, a receptacle in fluid communication with the isolated membrane for receiving the sample of liquid from the isolated membrane; and a test strip in fluid communication with the receptacle. The first and second members can be engaged with the membrane to isolate a portion of the membrane. The isolated portion of the membrane maintains a void volume substantially the same as the void volume of the unengaged membrane. The test strip detects the presence of analyte in the liquid sample. In one embodiment, the device further includes a control strip in fluid communication with the receptacle. The device can be used to detect the presence of an HIV antibody, an antibody to H. pylori antigen, or HCG antigen in the liquid sample.

In one embodiment of the device, a porous membrane is used to process and migrate a liquid to a dilution port zone. In the dilution port zone, the liquid saturated membrane is compressed circumferentially isolating a defined volume of sample within the isolated membrane. A specified quantity of diluent is then forced through the isolated volume of the membrane perpendicular to the direction of membrane lateral flow. The result is removal of the defined volume of liquid sample from the membrane and simultaneous dilution of the processed sample liquid. In another embodiment, the extracted sample liquid is directed through a narrow orifice that causes mixing of the diluent and production of a diluted sample. The diluted sample collects in a receptacle reservoir within the device that is in fluid communication with one or more membranes. These membranes can include diagnostic and control test strips positioned such that the diluted sample wicks from the receptacle well and migrates along each strip. Using such a methodology, the present invention provides a rapid diagnostic test that can be readily visually interpreted without a requirement for instrumentation.

In other aspects, kits for detecting an HIV antibody, an antibody to *H. pylori* antigen, or HCG antigen are provided. Each kit includes a device as described above and a container comprising a suitable diluent.

The present invention provides a method and device that permits processing, sampling, and reproducible dilution of processed and sampled fluids, and subsequent detection of analytes within the diluted fluid sample. In one embodiment, processing, sampling, dilution and detection are accomplished with a minimum number of user-friendly steps that produce a result within ten minutes. In one embodiment, the diagnostic result are lines that are clearly visible on a white background and that do not fade and are easily interpreted without instrumentation.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIG. 1 is an exploded perspective view of a representative device of the invention including a dilution port (10), a yoke (11), a cover (12), an o-ring (13), a midpiece (14), and a base (15);

FIG. 2A is a top plan view and FIG. 2B is a bottom plan view of dilution port (10);

FIG. 3 is a cross section view of dilution port (10) through its long axis hook arms (16) and channel (17) (the plane of the cross section and direction of sight are indicated in FIG. 2A);

FIG. 4A is a top plan view and FIG. 4B is a front elevation view of yoke (11);

FIG. 6A is a top plan view, FIG. 6B is a bottom plan view, and FIG. 6C is a front elevation view of midpiece (14) (the direction of sight for FIG. 6C is indicated by the arrow labeled 6C in FIG. 6A);

FIG. 8A illustrates a representative base (15), FIG. 8B illustrates a representative base (15) with midpiece (14), and FIG. 8B illustrates a representative base (15) with midpiece (14) and sample membrane (20);

FIG. 9B is a cross sectional view of the dilution port, sample membrane, o-ring, midpiece, base, and diagnostic test strip shown in FIG. 9A (the cross-section location and direction of sight of FIG. 9B is indicated in FIG. 9A);

FIG. 10A shows a valid negative result, FIG. 10B shows a valid positive result for antibody to HIV-1, FIG. 10C shows an invalid negative results due to an insufficient amount of blood tested, and FIG. 10D shows an invalid negative result due to a problem with the HIV-1 antigen;

DETAILED DESCRIPTION OF THE PREFERRED EMBODIMENT

The present invention relates to a method and device for processing, sampling, and diluting a fluid and to a method and device for detecting analytes within the processed, sampled, and diluted fluid.

In the method for processing, sampling, and diluting a fluid, an amount of a fluid is accepted by a porous membrane having a substantially uniform porous structure, and a portion of the membrane saturated with the fluid is isolated thereby defining a predetermined volume of fluid. The predetermined fluid volume is then released from the isolated membrane with a specified quantity of diluent to provide a diluted fluid sample. The device for diluting a fluid includes a membrane for accepting a fluid and a mechanism for isolating a portion of the membrane that is saturated with the fluid. When the diluted fluid includes an analyte, the invention provides a method and device for detecting one or more analytes in the fluid.

Figures 5A, 5B:
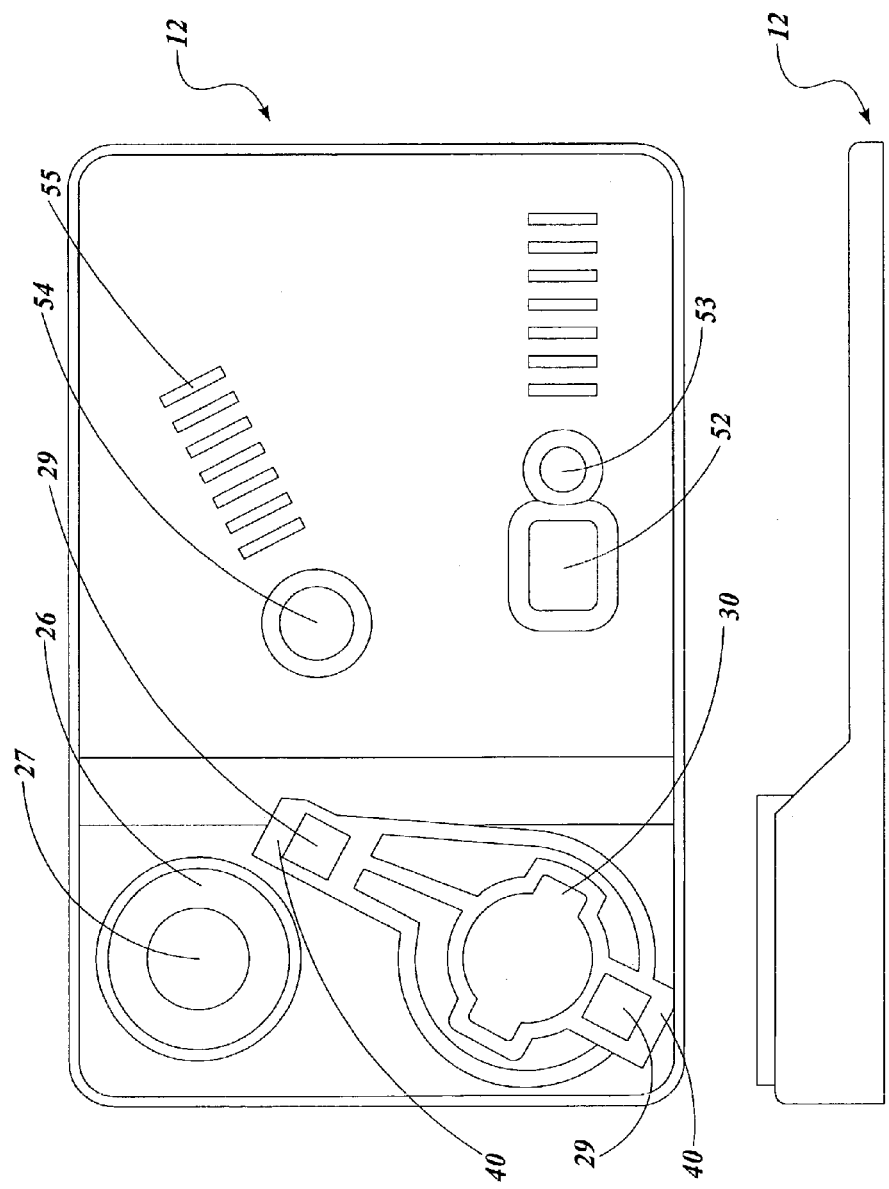
FIG. 5A is a top plan view and FIG. 5B is a front elevation view of cover (12)
Figures 7A, 7B:
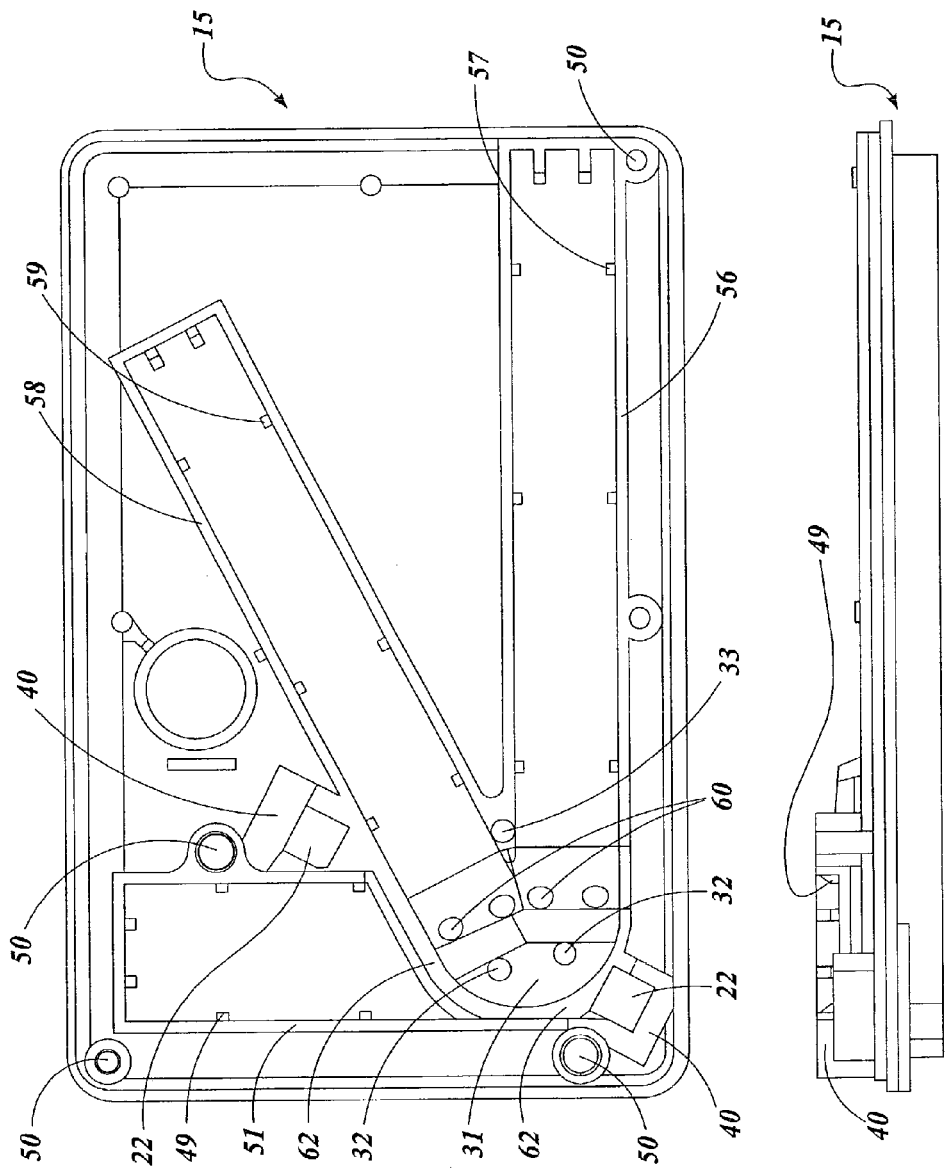
FIG. 7A is a top plan view and FIG. 7B is a front elevation view of base (15)

In one aspect, the present invention provides a method and device for processing, sampling, and diluting a liquid sample. The method can be carried out using the device illustrated in FIG. 1. Referring to FIG. 1, representative device 1 includes dilution port 10, yoke 11, cover 12, o-ring 13, midpiece 14, and base 15. FIGS. 2A and 2B illustrate dilution port 10. FIG. 3 is a cross section view of dilution port 10 through its long axis hook arms 16 and channel 17 (the plane of the cross section and direction of sight are indicated in FIG. 2A). FIGS. 4A and 4B illustrate yoke 11. FIGS. 5A and 5B illustrate cover 12. FIGS. 6A, 6B, and 6C midpiece 14 (the direction of sight for FIG. 6C is indicated by the arrow labeled 6C in FIG. 6A). FIGS. 7A and 7B illustrate base 15.

With reference to the illustrated device, in one embodiment, the method includes (a) adding a liquid sample to the sample collection well of the device, where the well is in fluid communication with a porous membrane; (b) saturating at least a portion the membrane with the liquid by waiting approximately two to three minutes for migration of the liquid sample along a membrane within the device, which in the case of whole blood separates serum or plasma at the leading edge of the membrane leaving behind cellular components; (c) isolating a portion of the membrane saturated with the liquid by depressing the dilution port of the device until it locks in place, thereby isolating a defined volume of the liquid-containing membrane; (d) releasing the isolated volume of liquid from the membrane with a diluent by inserting the tip of a provided vial into the depressed and locked dilution port to form a leak-proof seal, and squeezing the vial to deliver liquid through the dilution port, causing removal of the isolated volume of liquid from the defined isolated volume of membrane and forcing the liquid into a well located in the base of the device, simultaneously mixing the diluted sample; (e) migrating the diluted sample along one or more membranes, such as one or more diagnostic test strips and control test strips (migration time from about five to about seven minutes), and allowing a visually readable result to develop; and (f) interpreting the test and control results in the viewing windows of the test device.

The method and device of the invention permits detection of any analyte within a diluted liquid sample that is a member of a specific binding pair. A binding pair consists of two different molecules that through physical, chemical, or other means, specifically bind to each other.

The detection of antibodies to HIV by a representative method and device of the invention is described in Examples 7 and 8. The detection of antibodies to *H. pylori* antigen by a representative method and device of the invention is described in Example 9. The detection of HCG antigen by a representative method and device of the invention is described in Example 10.

The method of the invention can be further illustrated by reference to the device depicted in FIGS. 1-10. Referring to FIG. 5A, liquid sample to be diluted and analyzed is placed into receiving well 27. The well includes sloping sides 26 and a volume sufficient to collect more than liquid sample sufficient to allow completion of the test. The liquid may be placed into the receiving well with a disposable pipette, which results in a defined amount of liquid sample added to the device. Alternatively, an amount of liquid sample can be added in excess of the minimum amount required to complete the test. For example, the user may be instructed to add a volume sufficient to fully coat the membrane at the bottom of the receiving well and sufficient to coat the lower edges of the receiving well adjacent the membrane.

A membrane (see membrane 20 in FIG. 8C) is in fluid communication with the liquid sample received by the receiving well (see 27 in FIG. 5A) and transports at least a portion of the liquid sample from the receiving well to directly beneath the dilution port (see 30 in FIG. 5A).

The membrane transports at least a portion of the liquid to be diluted and tested from the first end of the membrane located beneath receiving well 27 to the second end of the membrane located beneath the dilution port (see 30 in FIG. 5A and 24 in FIG. 3) and above o-ring 13 contained within the upper surface the midpiece 14 (See FIGS. 1 and 6A).

The membrane allows transport of the analyte of interest. Ideally, the analyte does not bind to the membrane, such that analyte quantity is reduced. The membrane should not otherwise interfere with the analyte's accurate detection.

The membrane has a specified length, width, and thickness and a substantially uniform thickness, porous structure, and void volume. The membrane can be capable of being cut into precisely sized strips for use in the assay. Through its substantially uniform thickness and void volume, the membrane provides for a substantially constant amount of liquid contained within a given surface area (volume) of membrane.

In the practice of the invention, the membrane is compressible. The membrane's compressibility permits isolation of a portion of the membrane and collapse of the void volume in those portions of the membrane compressed between mating edges of dilution port 10 (see 24 in FIGS. 3 and 9B) and o-ring 13 (see FIG. 9B and FIGS. 6A and 6C). The noncompressed area of membrane 20 (see FIG. 9B) within the circumference of the ring of compressed membrane is thereby isolated and defines a specified volume of liquid sample.

The membrane allows diluent to flow through its thickness in the portion of membrane 20 (see FIG. 9B) isolated between the mating and compressing surfaces of the device noted above, thereby allowing release from the membrane and dilution for analysis.

Suitable membrane for use in the method and device are known in the art. Certain membranes may be more preferable for specific tests than others. For example, to separate red blood cells from a whole blood sample to produce a diluted sample of serum or plasma, suitable plasma separating membranes include those described by Baumgardner et al., U.S. Pat. No. 5,186,843. Alternatively, a membrane with suitable physical characteristics may be treated with a lectin or chemical to produce a plasma enriched sample for the membrane area isolated by the mating ridge and o-ring of dilution port and midpiece respectively. Bernstein et al. discuss this approach in U.S. Pat. No. 5,753,497. In other applications, the liquid sampling membrane may contain buffers, reagents, and molecules to protect the analyte of interest from loss on the membrane, or any other adaptations that promote the performance of the membrane and optimize the ultimate detection of the analyte of interest.

Sample receiving or collection pads can be mated to the sample transporting membrane. Sample receiving and collection pads are described by Pawlak et al., in U.S. Pat. No. 5,770,460. The sample receiving or collection pad can include reagents to optimize the test performance.

A representative device of the invention that facilitates compression of a circumscribed area of membrane thereby isolating a membrane volume centripetal to the mating compressing edges of the device is illustrated in FIGS. 1-10. Referring to FIGS. 1, 7A, and 8B, representative device 1 includes channel 28 (FIG. 8B). for receiving sample membrane 20 (FIG. 8C) that aligns the membrane between opposing surfaces of dilution port 10 and midpiece 14. Dilution port 10 (FIG. 1) is held in alignment within cover 12 by hook arms 16 (see FIG. 3) that fit within hook arm channels 29 (FIG. 5A). The rectangular protrusions of the dilution port (FIG. 1) can only fit in one orientation to match corresponding portions of cover (see 30 in FIG. 5A). This fit also helps to maintain alignment and stability of the device. Midpiece 14 (FIG. 1, FIG. 6A, FIG. 6B and FIG. 8B) is held in alignment with base 15 by guide pegs and matching surfaces. Guide pegs 32 (FIG. 7A) within receiving well 31 of base 15 and guide peg 33 (FIG. 7A) protrudes upward from the junction of the channels in the base, which hold the diagnostic membrane 18 (FIG. 8A) and control membrane 19 (FIG. 8A). Guide pegs 32 mate with receptacles 34 (FIG. 6B) on the undersurface of midpiece 14. Guide peg 33 (FIG. 7A) passes through aperture 35 (FIGS. 6A and 6B) in midpiece 14 and inserts into a mating receptacle on the undersurface of cover 12 (not shown). O-ring 13 (FIG. 1) is received within channel 36 (FIGS. 6A and 6C) in midpiece 14, which holds approximately 70% of the o-ring volume within the channel. Channel 36 provides a friction fit that prevents loss of the o-ring from the midpiece during assembly, and allows approximately 30% of the o-ring to protrude above the upper lip of. the channel (see FIG. 6C). As noted above, O-ring 13 is compressible and serves to maintain compressive force on the sample membrane between it and surface 24 of dilution port 10 (see FIGS. 3 and 9B). The alignment and stability of the dilution port and midpiece with o-ring in its upper surface facilitate delivery of a compressive force to a circular perimeter of sample membrane.

Yoke 11 (FIG. 1) prevents dilution port 10 from being accidentally depressed and locked into the bottom piece and thereby preventing flow of the sample along the sample membrane for testing. Yoke arms 37 (FIG. 4A) fit into matching slits 70 (FIG. 3) of dilution port 10. Yoke arms 37 and yoke side arm 38 (FIGS. 4A and 4B), which fits beneath the long arm of the dilution port, prevent the dilution port from being depressed into the device until the yoke is removed.

The invention provides a device that provides a user-friendly means to effectively initiate and maintain the compressive force on a circumscribed area of membrane. A representative device is shown in FIG. 1. To operate the device, yoke 11 (FIG. 1) is grasped by handle 39 (FIGS. 4A and 4B) and pulled to slide arms 37 away from mating slits 70 of dilution port 10. With the yoke in this position, dilution port 10 can be pressed downwardly into the device. The downward force compresses membrane 20 between the undersurface ridge 24 of dilution port 10 and o-ring 13 (see FIG. 9B). With further downward force, o-ring 13 is compressed allowing hooks 21 (FIG. 3) at the ends of hook arms 16 (FIG. 3) of dilution port 10 to lock into place with base 15 through receptacles 22 (FIG. 7A). Ridges 40 (FIG. 7A) adjacent the hook arm receptacles 22 lock the hooks of the dilution port hook arms in place. The hook arms maintain the alignment and stability of dilution port 10, and the alignment of midpiece 14 is maintained by matching guide pegs and receptacles and matching surfaces between the midpiece and base. The compressive force on the membrane is maintained by the depressed and locked-in-place dilution port, and by the resistance to compression of the o-ring. This effectively isolates the portion of membrane centripetal to these mating surfaces with minimal effort or complexity for the user. Fluid added to the membrane within this isolated area tends to move vertically through the membrane thickness and does not easily pass through the compressed areas to escape laterally along the membrane. Other methods that introduce and maintain compressive force to isolate a circumscribed volume of the membrane are also be within the scope of this invention. Any two surfaces that effectively mate and compress a perimeter area of membrane to isolate a portion of membrane within that perimeter are included within the scope of this invention. The compressing surfaces are not limited to the o-ring and plastic surfaces illustrated in the representative device depicted in the drawings.

The invention provides a device that facilitates introduction of a defined amount of diluent to an isolated area of membrane to be sampled. This can be accomplished with minimal effort and complexity by the user when using the device illustrated in FIGS. 3 and 9B. Dilution port 10 includes channel 17 that traverses vertically through the port (see FIGS. 2A, 2B, and 9B). Channel entrance 42 can be adapted to mate with a diluent vessel. Entrance 42 can be mated with the neck of a commercially available vial having a twist-off top. The vial can be economically manufactured in bulk and prefilled with defined amounts of sterile buffered diluent. These vials can be compressible and their necks designed so that liquid does not escape from the vial when the cap has been twisted off and the vial is inverted. The neck of the inverted vial can mate to form a leak-proof seal with the tapering sides 41 of the entrance to dilution port channel.

The device described above allows for delivery of a defined amount of liquid diluent under pressure as follows: (1) the dilution port is pressed down into its locked position as described above to isolate an area of membrane containing a sample to be diluted; (2) the cap of the compressible vial is removed, the vial inverted, and its neck placed into the mating entrance channel of the dilution port to form a leak-proof seal; (3) the vial is compressed delivering under pressure a defined amount of diluent through the channel 17 in dilution port 10 to the isolated area of sample membrane 20s (FIG. 9B).

The invention provides a device that provides for a flow of diluent though the isolated area of membrane to be sampled, simultaneously removing the sample from the membrane and diluting the sample, and directing the diluted sample away from the membrane. Midpiece 14 includes channel 23 (FIGS. 6A, 6B, and 9B) that passes vertically through the midpiece having entrance 44 (FIG. 6A). Channel 23 directs diluent fluid that passes through the isolated membrane. When diluent fluid is delivered under pressure to the isolated membrane as described above, diluent passes through the isolated area of membrane and away from the membrane through the vertical channel in the midpiece. The result is simultaneous removal and dilution of the sample contained within the isolated volume of sample membrane and exit of this diluted sample from the undersurface of the midpiece.

Figure 9A:
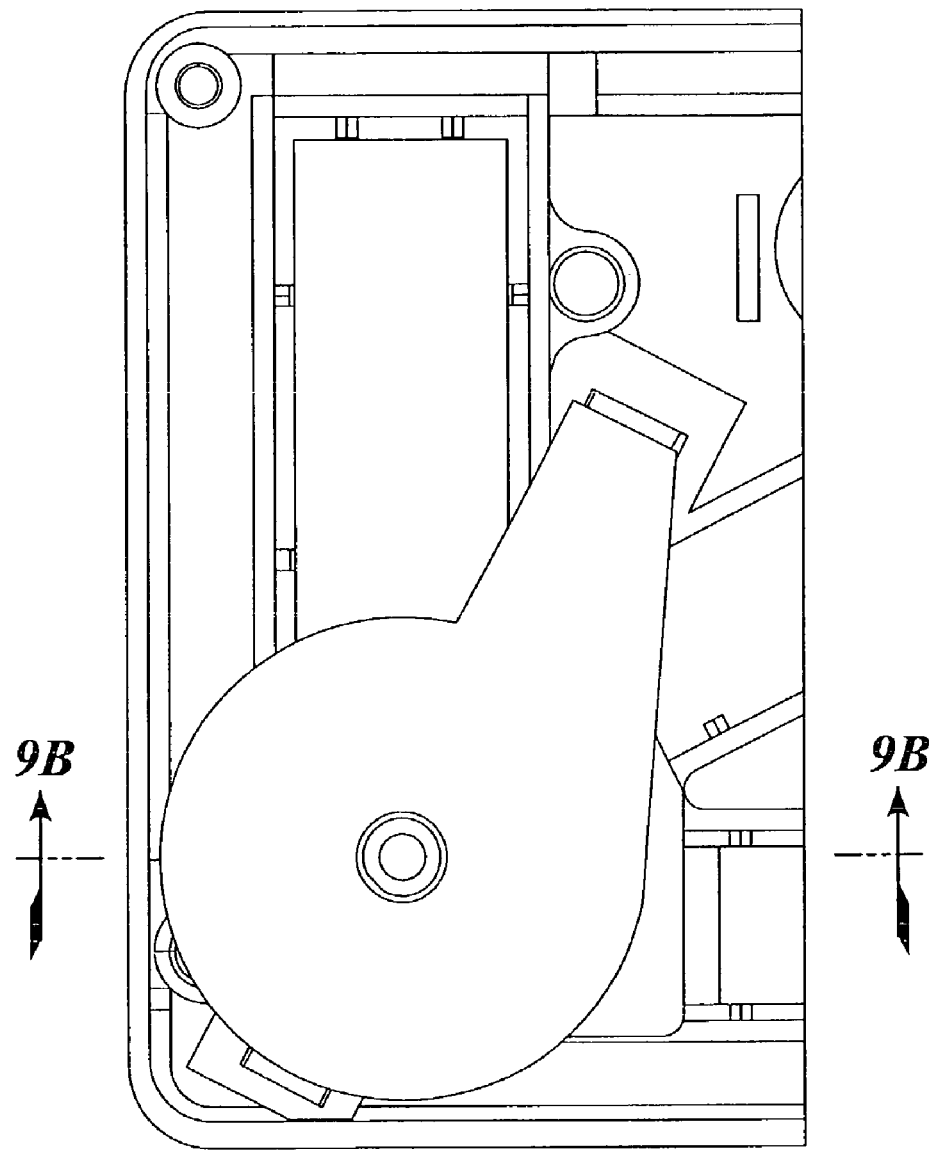
FIG. 9A is a top sectional view of the dilution port, sample membrane, o-ring, midpiece, base, and diagnostic test strip, when the dilution port is depressed into the locked position compressing the sample membrane in a representative device of the invention.
Figure 10A:
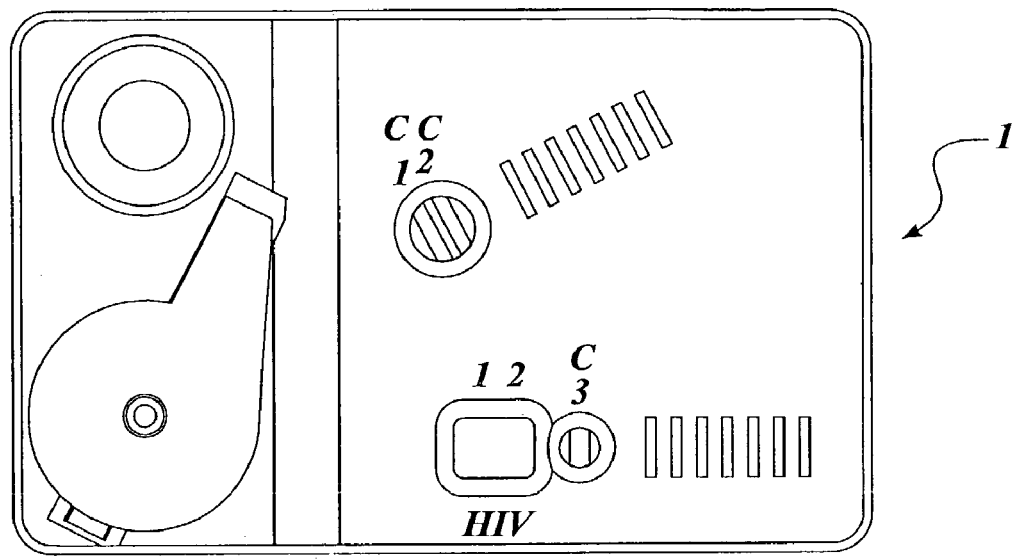
FIGS. 10A, 10B, 10C, and 10D are top views of a representative device of the invention showing visual results obtained by the method and device of this invention to detect antibodies to HIV.
Figure 10B:
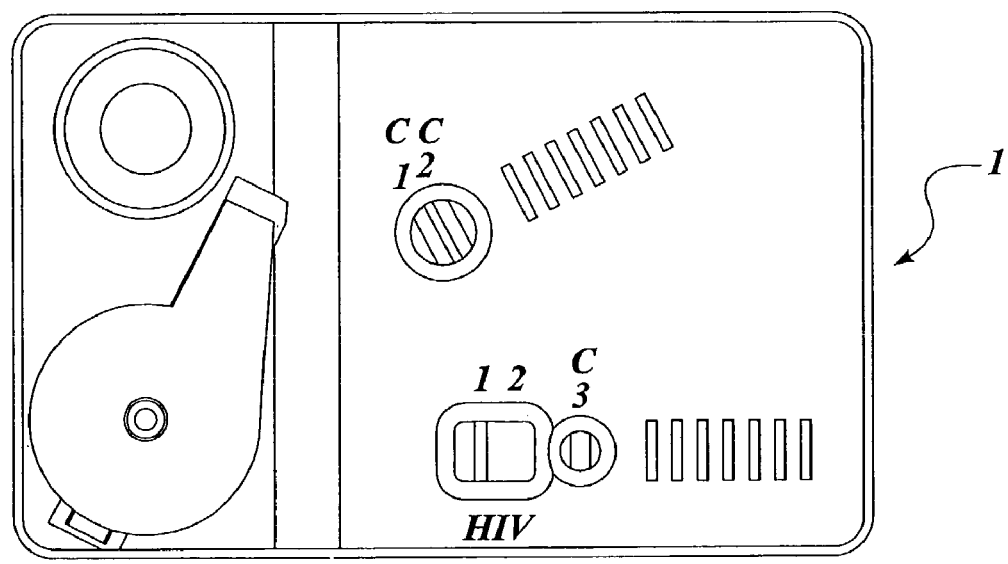
Figure 10C:
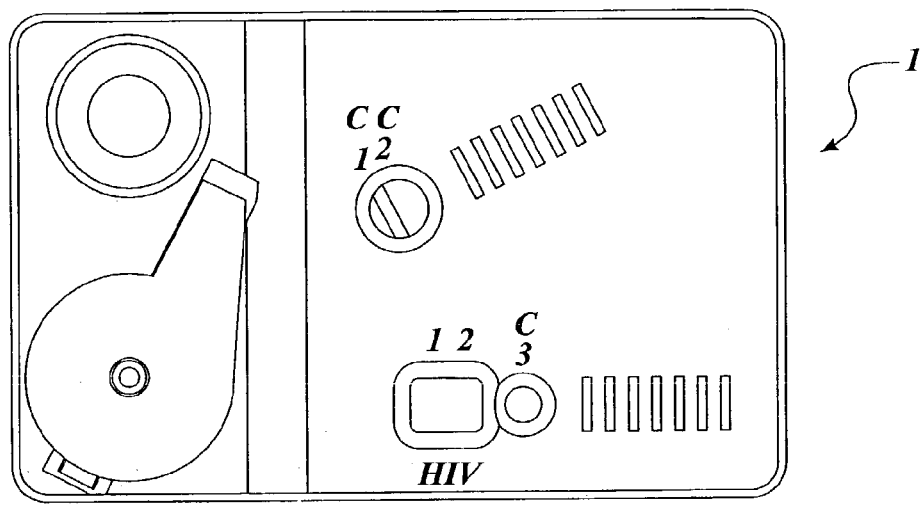
Figure 10D:
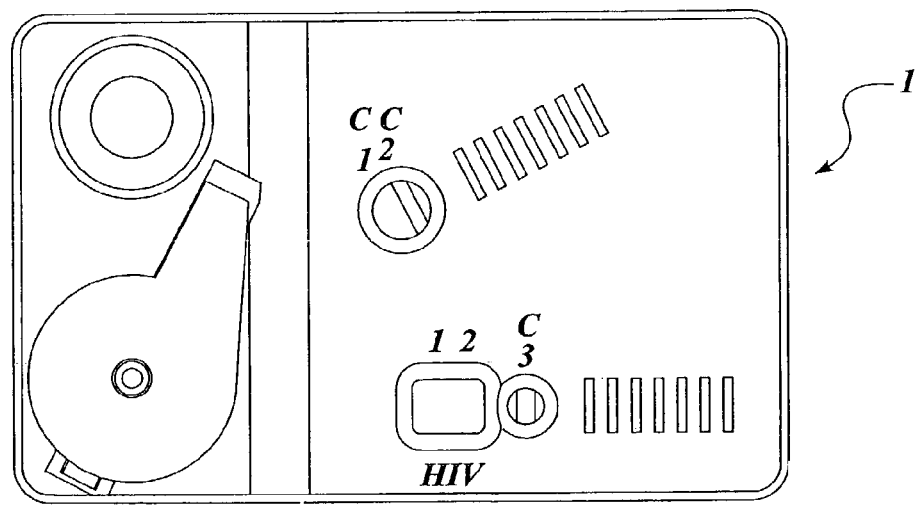

The device of the invention provides for mixing of sample and diluent to deliver a relatively uniform dilution of sample that is collected in a well within the device. The wicking uptake ends of diagnostic and control test strips, which allow for the evaluation of the presence or absence of analytes within the diluted sample, terminate in the well. Referring to FIGS. 1, 7A, and 9A, when diluent is delivered to the isolated membrane, the sample within the isolated membrane is washed out and passes through channel 23 in the midpiece and exits to reservoir well 31 in base 15. Reservoir well 31 holds all of the diluent introduced into the device. The amount of diluent introduced is sufficient to effect complete wicking to the end of both strips (diagnostic and control) in the device. The delivery of diluent through the isolated membrane, its passage through the narrow channel of the midpiece, and rapid flow to the reservoir well results in mixing action that produces a relatively uniform dilution of sample for analysis. The diluent may be pressurized and delivered under pressure.

Figure 8A:
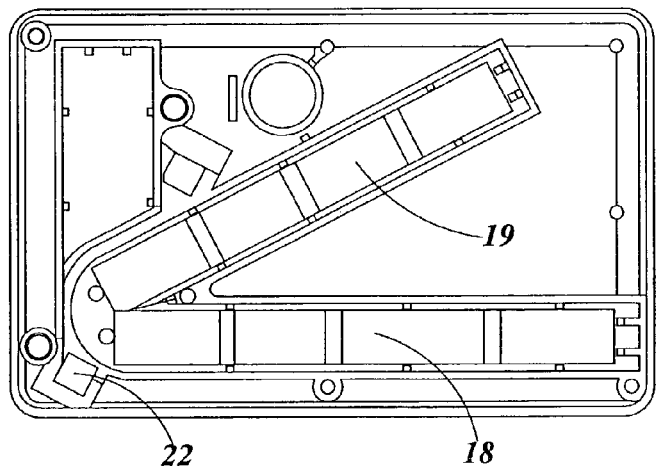
FIGS. 8A, 8B, and 8C are top plan views of base (15) of a representative device of the invention.

As noted above, the device of the invention includes a reservoir well that collects the diluted sample and facilitates capillary wicking of the diluted sample into diagnostic and control test strips. Passage of the diluted sample along the diagnostic and control strips permits evaluation of the presence or absence of analyte. Referring to FIGS. 1, 6C, 7A, 8A, 8B, and 9B, channels 56 and 58 (FIG. 7A) and guide pegs 57 and 59 (FIG. 7A) hold diagnostic strip 18 and control strip 19 (FIG. 8A). Guide pins 32 for the midpiece project upward from reservoir well 31 and serve to locate the wick end of the test strips. During assembly of the device, the wicking ends of the diagnostic and control test strips are depressed to the bottom of the reservoir well in the base by projections 47 and 48 on the undersurface of the midpiece (FIGS. 6B and 6C). Some of these projections hold the wick portion of the diagnostic and control strips at the deepest portion of the reservoir to ensure access to the entire diluted sample. Other guides on the undersurface of the midpiece as well as on the undersurface of the top piece (not shown) hold the strips in place within the channels.

A cross-sectional view of a the assembled device is illustrated in FIG. 9B. The plane and direction of sight of the cross-section are indicated in FIG. 9A. The cross-sectional surface of each part is indicated by its part number followed by the letter "s". Specifically, the sectional surface of the dilution port is 10s, and the sectional surfaces of the sample membrane, o-ring, midpiece, base, and diagnostic test strip are 20s, 13s, 14s, 15s and 18s, respectively. With the dilution port depressed and locked into position, the sample membrane is compressed between undersurface 24 of the dilution port and the uppersurface of the o-ring 13 contained within the midpiece. This results in isolation of the sample membrane contained within the perimeter of the o-ring. Liquid applied through the dilution port channel 17 exits onto a diameter of membrane equivalent to the diameter of the dilution port exit 43. This liquid does not escape along the sample membrane 20, but instead passes perpendicularly through the sample membrane (i.e., through its thickness) due to lower resistance. This flow of liquid through the isolated portion of the sample membrane removes sample contained within the void volume of the sample membrane. The removed sample and associated diluent fluid passes to channel 23. Sample and diluent also passes into the four collection areas of the midpiece 44 that empty into the central through-channel. These collection areas are located between the four membrane support posts 46 at the top of the midpiece immediately beneath the area of membrane sampled. The removed sample and diluent mix as they pass by the collection areas into channel 23 and collect in receptacle well 31 of the base. This diluted sample is then wicked from the receptacle well along the diagnostic strip 18 and the control strip 19 (not shown) to evaluate for the presence of analyte.

Figure 8B:
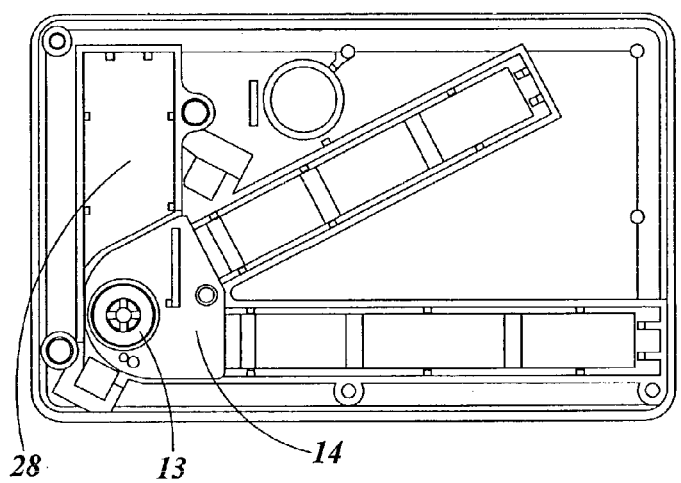
Figure 8C:
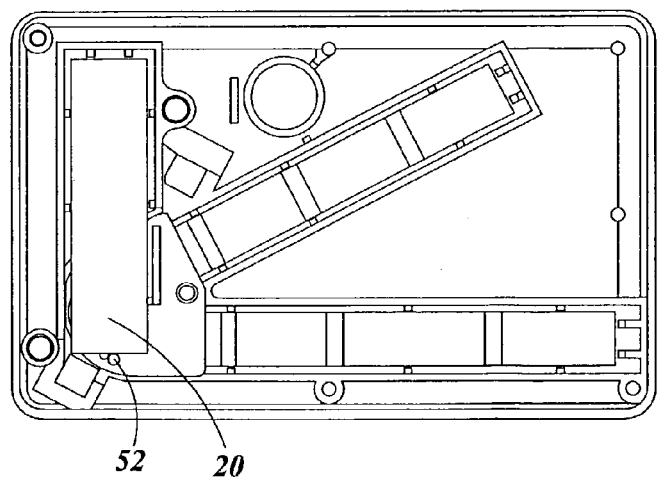

The device of the invention can be made by automated assembly. Assembly can be made as follows: base 15 lays flat on a pallet and is ready to receive diagnostic and control strips, and optionally a desiccant tablet. These strips are held in place by the channel guides 56 and 58 and pegs 57, 59, and 32 (FIG. 7A). Midpiece 14 with o-ring 13 in place is added to the assembly guided by pegs 32 and 33 that project upward from base 15. With the addition of the midpiece to the assembly, the diagnostic and control test strips are held in place within the base, and channel 28 (FIG. 8B) for receiving sample membrane 20 (FIG. 8C) is formed by the base and adjacent midpiece. Sample membrane 20 is then added to the assembly, and held in piece by channel guides 49 and 51 (FIG. 7A) and stop peg 52 (FIG. 8C). Cover 12 is then added and held onto the bottom piece by mating pegs and tapered receptacles 50 (FIG. 7A) that allow a secure press-fit between the two parts. Yoke 11 is connected to dilution port 10 by sliding yoke arms 37 (FIG. 4A) into matching slots 70 of dilution port 10. The combined dilution port and yoke is then fitted to the assembly by placing hook arms 16 of the dilution port into hook arm receptacles 29 (FIG. 5A). The dilution port is held in place against removal from the top piece by hooks 21 (FIG. 3) on the hook arms which rest against the undersurface of ridges 40 (FIG. 5A). The dilution port is prevented from depression into a locked position in the bottom piece until the user removes the yoke prior to conducting the test.

The method and device of the invention can be used for testing multiple analytes and allows for internal quality controls on the reagents used in each test. As shown in FIG. 8A, two strips enter the reservoir well permitting the diluted sample to flow over the diagnostic test and control strips. In other embodiments, the device can include more than two strips contacting the same reservoir well.

FIGS. 10A, 10B, 10C, and 10D illustrate the use of the method and device of the invention in a rapid test for antibodies to HIV. An internal control is used to assess whether a sufficient amount of serum immunoglobulin has been added to the test (C3). In addition, control wells C1 and C2 monitor the integrity of two separate synthetic peptide-protein conjugates that are use to detect antibodies to HIV-1 (C1) and HIV-2 (C2). Without all of these controls, one is less certain that a negative result for antibodies to HIV-1 and HIV-2 represents a true negative. One could not conclude that a negative result is due to the absence of antibodies to HIV in the test sample rather than loss of integrity of HIV antigens, unless these internal controls for HIV-1 antigen (C1) and HIV-2 antigen (C2) are included and demonstrate that these antigens are intact. A negative result is also not definitive without knowing that sufficient immunoglobulin was tested. If an individual adds diluent prematurely to the dilution port and initiates the wicking through the diagnostic test strip before any sample has reached the area beneath the dilution port, a potentially false negative result would not be detected without control (C3) that confirms sufficient immunoglobulin has been evaluated. The diagnostic test strip used in this example also permits simultaneous determination of whether a sample positive for antibodies to HIV contains antibodies to HIV-1, HIV-2 or both. Currently available diagnostic tests using lateral flow technology usually include controls to confirm sufficient immunoglobulin has been tested, but no currently available tests include internal controls of antigen integrity.

In summary, in one embodiment, the invention provides a method and a device, as exemplified in FIGS. 1-10, that provides for testing for specific analytes within a collected and diluted sample, both without need of instrumentation or formal training.

A representative device of the invention includes five components: (1) dilution port; yoke; cover; midpiece, and base.

The device's cover includes a sample receiving well for collecting a sample liquid to be tested and allowing the sample to contact and fill the voids of a sample membrane (sample membrane). The device's base includes a channel to contain the sample membrane and provide fluid communication between the receiving well and the dilution port. The sample membrane transports liquid from the receiving well to the dilution port. Depending on the application, the sample membrane can include components that prepare or modify the sample for subsequent testing. The sample membrane is porous and contains the sample within its voids and allows the sample to be subsequently removed from a defined volume of membrane isolated by the device.

The dilution port, which fits into prescribed portions of the cover and base, is held in a non-active position on the top piece by a yoke, which slides into grooves of the dilution port thereby preventing it from being depressed down into the device, thus allowing free passage of the test liquid in the sample membrane without obstruction from any surfaces of the dilution port. When the yoke is removed, the dilution port may be depressed into the active position and catch hooks on the tension arms of the dilution port lock into place against catch receptacles causing the flat circular undersurface of the dilution port to compress the area of the sample membrane between the dilution port and a matching circular upper-surface of an o-ring contained within the midpiece. The compressed membrane effectively prevents any substantial flow of liquid along the membrane either from outside or inside the area circumscribed by the corresponding mating surfaces of midpiece o-ring and dilution port.

The midpiece includes a top surface completes the channel that confines the sample membrane and contains a groove to hold the o-ring that forms one mating surface with the dilution port to define the volume of sample membrane for testing. The midpiece includes a through-channel to allow passage of diluent and sample out of the sample membrane and down into the reservoir located in the bottom piece. The undersurface of the midpiece includes protrusions that guide the diagnostic and control membranes into the reservoir to allow analysis of the diluted sample.

The device's base includes components for alignment with the midpiece and cover and catch receptacles for the hook arms of the dilution port to lock the port and base into the active position. The base includes one or more channels that contain test and/or control strips and a channel for the sample membrane. The test and control strip channels permit the test and control strips to contact the diluted test sample in the reservoir well, and further align the strips to pass by viewing windows for test result analysis.

The test and control strips contact the diluted sample in the reservoir well. The sample migrates out of the reservoir along the strip and encounters a microparticle pad that contains visible particles that bind to and label the analyte of interest. The migrating labeled analytes of the diluted sample then bind to defined areas of the strip, located beneath view windows (see FIG. 10 circular and rectangular viewing windows). Any migrating fluid not bound to one of the membranes of the test or control strips is then absorbed by blotters bringing the test reaction to completion and ready for reading (see FIG. 10 example);

Control strips or reagent lines confirm reactive potency of the reagents used in the test (see, for example, FIG. 10, C1 and C2) and confirm that the diluted sample is adequate for testing (see, for example, FIG. 10, C3).

In another aspect, the invention provides a system that includes, in addition to the device, a vial that contains the precise volume of dilution reagent required for a given test. In one embodiment, the vial is compressible and further includes a volume of gas equal or greater than the contained liquid. The vial includes a neck having a sufficiently small diameter to prevent leakage of the solution when the bottle is inverted and having a tip of appropriate size and malleability to form a tight seal when placed into dilution port vial tip receptacle. With the cap removed and the neck of the vial placed firmly into the vial tip receptacle of the dilution port, squeezing the vial forces out all of the liquid from the vial and down through the dilution port. A channel in the dilution port connects the dilution port vial tip receptacle with the undersurface of the dilution port and the area of isolated sample membrane. The mating surfaces of the port and midpiece define a circumscribed volume of sample membrane. When a known volume of dilution reagent is passed through this volume of membrane, the sample liquid in the membrane is removed and diluted in a reproducible fashion.

In another embodiment, the invention provides a method for easily and reliably sampling a test liquid, and; in some instances simultaneously diluting that test liquid. The method includes filling the voids of a porous membrane with a liquid sample; isolating a defined amount of the liquid sample within the voids of the sample membrane; and releasing the defined amount of sample liquid from the membrane.

The liquid sample is isolated by opposing two complementary surfaces on opposing major surfaces (i.e., on either side) of the sample membrane. These complementary surfaces form a perimeter around a defined volume of the membrane. The isolated liquid sample can be removed from the membrane by delivering a second liquid or gas to the portion of the membrane containing the isolated liquid sample. When a second liquid is used, the liquid sample is simultaneously diluted.

The liquid sample released (and diluted) from the membrane is collected into a reservoir where it can be further analyzed to detect specific components or analytes.

The representative device of the invention illustrated in FIG. 1-10 was designed using modeling, computer-aided design. The 3-D modeling and computer aided design program Rhinoceros, copyright 1993-1998, Robert McNeel and Associates, Seattle, Wash., USA, was first used as a beta version, and later as a commercially available software application. Once a design was completed, an STL file was created and provided to several different rapid prototypes were produced using stereolithography. In some instances, critical portions of the parts were machine-tooled to achieve desired tolerances. Test results are presented in the following examples.

The following examples are intended to illustrate but not limit the scope of this invention.

EXAMPLE 1

Reproducibility of Dilutions of Test Sample

CytoSep 1661 membrane was obtained from Ahlstrom Filtration Inc., Chattanooga, Tenn. (see U.S. Pat. No. 5,186,843, Baumgardner et al., Blood Separation Media and Method for Separating Plasma From Whole Blood). Single-sided adhesive coated polyester from Adhesives Research Inc., Glen Rock, Pa. (ARCARE 7815) was laminated to portions of both sides of the CytoSep 1661 membrane prior to sizing the strips to fit channel 51 shown in FIG. 7A of the medical device. This impermeable polyester sheet served to confine the liquid flow to within the membrane, and not over surfaces of the device in those areas where it was applied. After lamination with polyester, strips 20 (FIG. 8C) were cut to size to fit channel 51 shown in FIG. 7A. Each sized strip of CytoSep 1661 contained on its undersurface laminated polyester. This polyester extended from the end of the strip that rests beneath the sample receiving well in the fully assembled device along the undersurface up to approximately two millimeters short of the outer margin of the o-ring contained within the midpiece (see FIG. 8B). The upper surface of each sized CytoSep 1661 strip contained laminated polyester beginning approximately 2 mm beyond the downstream edge of the undersurface of the device sample receiving well 27 (FIG. 5A) to 2 mm short of the outer margin of the o-ring 13 contained within midpiece 14 (FIG. 8B). For purposes of this example size 008 o-ring and a midpiece designed to tightly hold size 008 o-ring were used. The sized and laminated CytoSep membrane strip was placed into the device and all five plastic components of the device were assembled before use.

Schilling™ Red food coloring (manufactured by McCormick & Co, Inc., Hunt Valley, Md., and containing FD&C Reds 40 and 3) was obtained from a local supermarket. A stock 1:10 dilution of the food coloring was prepared in PBSAA buffer consisting of 50 mM phosphate, 10 mM NaCl, pH 7.4, and 0.05% sodium azide and 0.1% bovine serum albumin in deionized water. Dilutions of this stock solution were scanned with a Gilford spectrophotometer (Gilford Systems, Ciba Corning, Oberlin, Ohio). Peak absorbance was noted at a wavelength of 495 nanometers.

Experiments to test the reliability of the device to produce a consistent dilution of the stock solution of red food coloring were conducted as follows. Approximately two drops (100 to 120 microliters) of the stock solution were added to the fully assembled device containing the sized and laminated CytoSep 1661 membrane. After a wait of two minutes, the yoke was removed from the dilution port, and the dilution port was pressed down into the locked position. A twist-off capped plastic 0.8 ml vial, obtained from Automatic Liquid Packaging, Woodstock, Ill., and prefilled with 450 microliters of PBSAA buffer diluent, was inverted and its neck was pressed into the entrance to the channel in the dilution port to form a leak-proof seal. The vial was squeezed to express all of its contents, held for 3 seconds, and then removed while keeping the vial squeezed.

Buffer diluent passed through the portion of CytoSep 1661 membrane isolated for testing by the device. This isolated membrane consisted of the noncompressed circular area of membrane located within the circumference of a ring of membrane compressed by the device. The ring of membrane compression was produced by the undersurface of the dilution port in the locked and active position and the o-ring held in the upper surface of the midpiece. Buffer diluent introduced under pressure into the dilution port channel passed through this channel and through the isolated ring of membrane removing the red food coloring. The extracted red food coloring and diluent passed down through the channel in the midpiece resulting in a mixed dilution of sample that collected in the reservoir in the bottom piece.

The dilution of the red food coloring achieved by the device was assessed as follows.

Immediately after expressing the diluent from the twist-off cap vial and removing it from the device, the dilution port was unlocked, and 300 microliters of diluted sample was removed from the reservoir and placed into a test tube. To each 300 microliters of diluted sample was added an additional 300 microliters of PBSAA diluent for purposes of reading the result in the spectrophotometer cuvette. This resulted in a 1:2 dilution of the dilution produced by the device. The device was used repeatedly to evaluate dilutions that it produced of the red food coloring stock solution under different conditions. The dilutions achieved were evaluated by reading the 1:2 diluted samples at a wavelength of 495 nanometers.

Figure 11A:
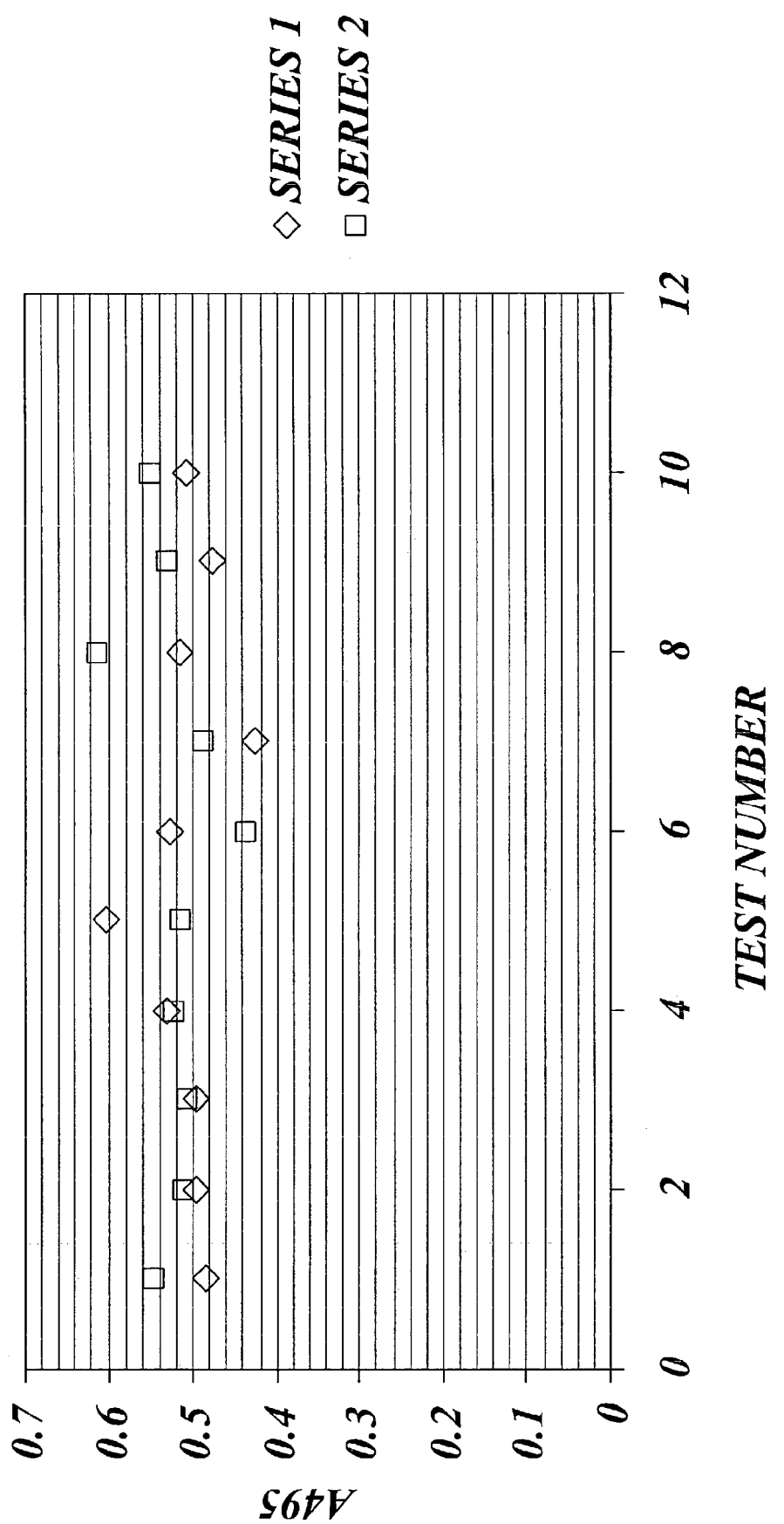
FIGS. 11A and 11B are graphs illustrating the reproducibility of dilutions obtained in two series of tests using a representative method and device of the invention.
Figure 11B:
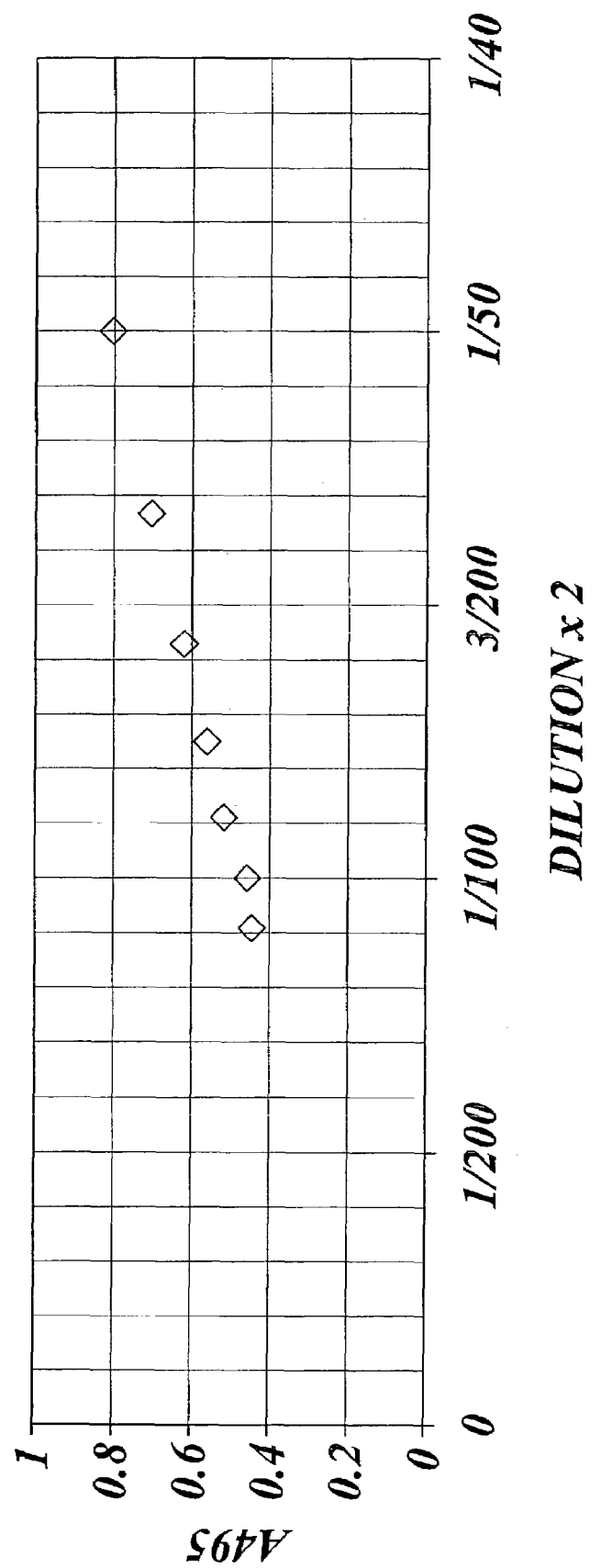

FIG. 11A presents the mean absorbance at 495 nm wavelength of two separate sets of ten dilutions each performed on separate days using the medical device with CytoSep 1661 membrane and a size 008 o-ring in the midpiece. The mean absorbance was 0.515 and the median absorbance was 0.514. The range of two standard deviations from the mean was 0.425-0.605. When compared to a standard curve developed from known dilutions of the stock solution read under the same conditions, the two standard deviations range of dilutions produced by the device was 1/75 to 1/105 (FIG. 11B).

EXAMPLE 2

Role of Sample Membrane Thickness on Dilution

Figure 12A:
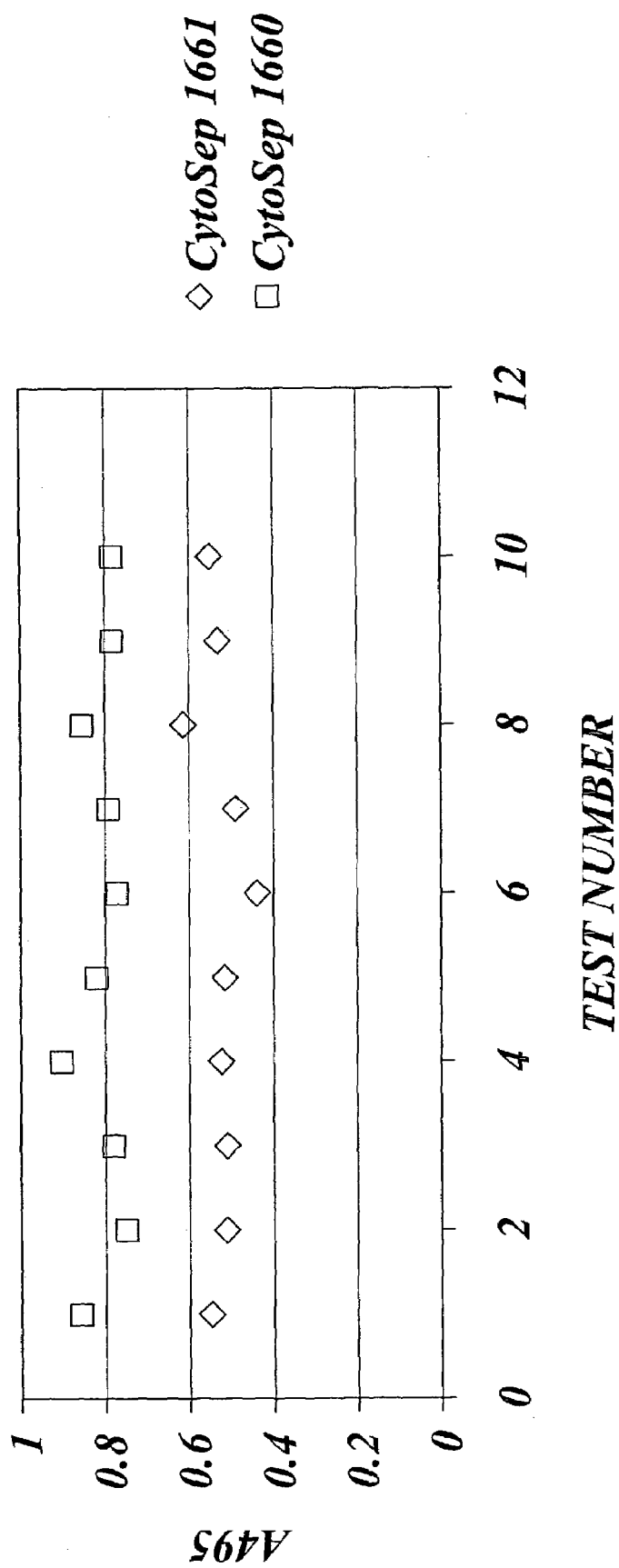
FIGS. 12A and 12B are graphs illustrating the effect of membrane thickness and sample-holding capacity of the sampling membrane on the amount of sample obtained for analysis by a representative method and device of the invention.
Figure 12B:
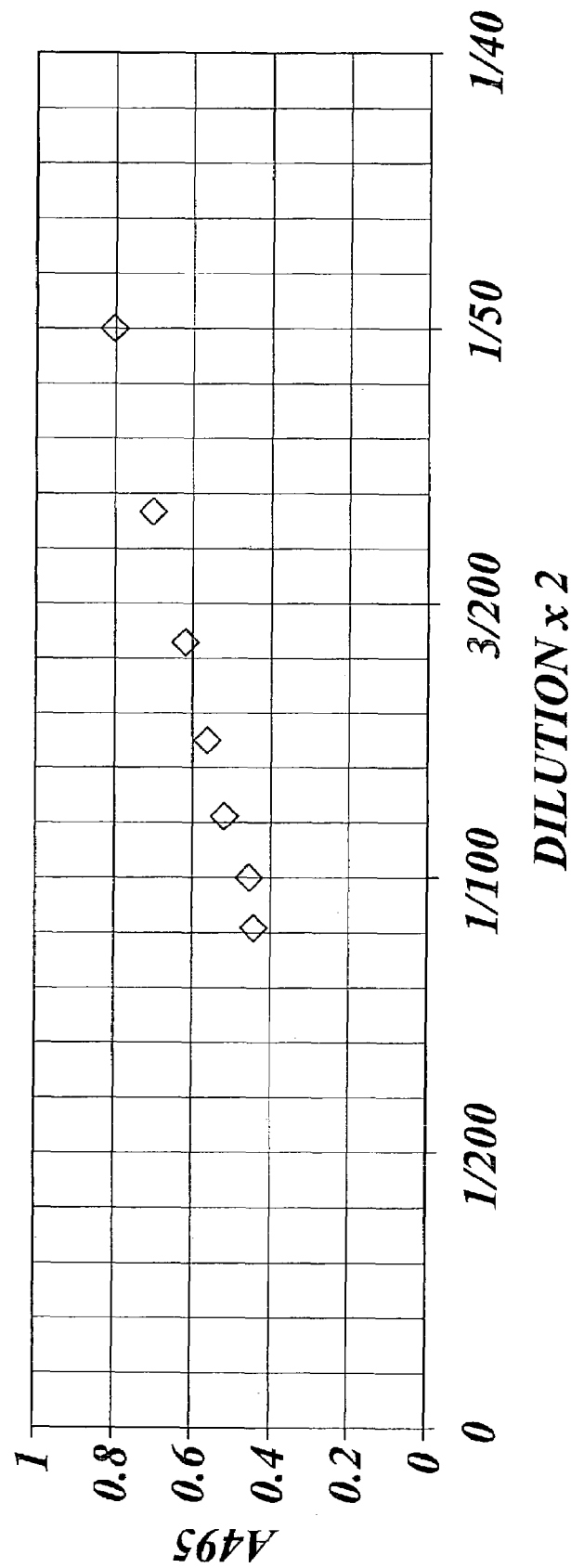

FIG. 12A presents the mean absorbance at 495 nm wavelength of two separate sets of ten dilutions each performed on separate days using the medical device and a size 008 o-ring in the midpiece. For one set of ten dilutions CytoSep 1661 with a thickness of 0.18 mm was used, and for the other set CytoSep 1660 with a thickness of 0.33 mm was used. Three drops of stock solution (approximately 165 microliters) was used with the CytoSep 1660 membrane because of its capacity to hold a greater volume of sample. Two drops (100 to 120 microliters) of the stock solution were added to the sample receiving well for the series using CytoSep 1661. In both series the volume added fully saturated the void volume of the membranes used. The average dilution produced with the CytoSep 1661 membrane was 1/90 with a two standard deviation range of 1/75-1/105. The average dilution produced with the CytoSep 1660 membrane was 1/50 with a two standard deviation range of 1/44 to 1/65 (FIG. 12B). This illustrates that a range of dilutions can be obtained using the method and device of this invention by selecting membranes of different thickness. Those membranes that are thicker will contain more sample per unit area, and hence result in a lower dilution produced by a given quantity of diluent.

EXAMPLE 3

The Effect of Membrane Surface Area Sampled on Dilution

Tests were performed as in Example 1 using CytoSep 1661 membrane. One hundred microliters of red dye solution were added to the receiving well. Four hundred fifty microliters of PBSAA diluent were added to remove sample from the circumscribed isolated CytoSep 1661 membrane, after a two minute delay between adding red dye stock solution to the receiving well and adding diluent through the dilution port. Triplicate dilutions were performed with a size 008 o-ring with an internal diameter of 4.55 mm, and compared with triplicate dilutions performed using a dilution port and midpiece designed for use with a size 007 o-ring which has an internal diameter of 2.55 mm. Using the formula $\pi r^2$ it can be seen that the comparison of surface areas sampled by the two o-rings is surface area 008/surface area 007=$(2.275)^2/(1.275)^2$=5.18/1.63=3.18. One therefore expects that the device and method would remove 3.18 times more sample using the 008 o-ring. Triplicate tests using the 008 membrane produced A495 readings of 0.447, 0.423, and 0.445, for a mean A495 of 0.438. The triplicate tests using the 007 o-ring produced A495 readings of 0.226, 0.184, and 0.212, for a mean A495 of 0.207. The 0.438 mean A495 reading corresponds to a 1/120 dilution, and the mean A495 of 0.207 corresponds to a dilution of 1:380, when applied to the standard curve of dilutions obtained known dilutions of the stock red dye solution (FIGS. 11B and 12B). The ratio of these two dilutions is 380/120=3.17, close to the predicted result based upon surface area sampled.

EXAMPLE 4

Effect of Volume of Sample Placed into Receiving Well on Dilution

Figure 13:
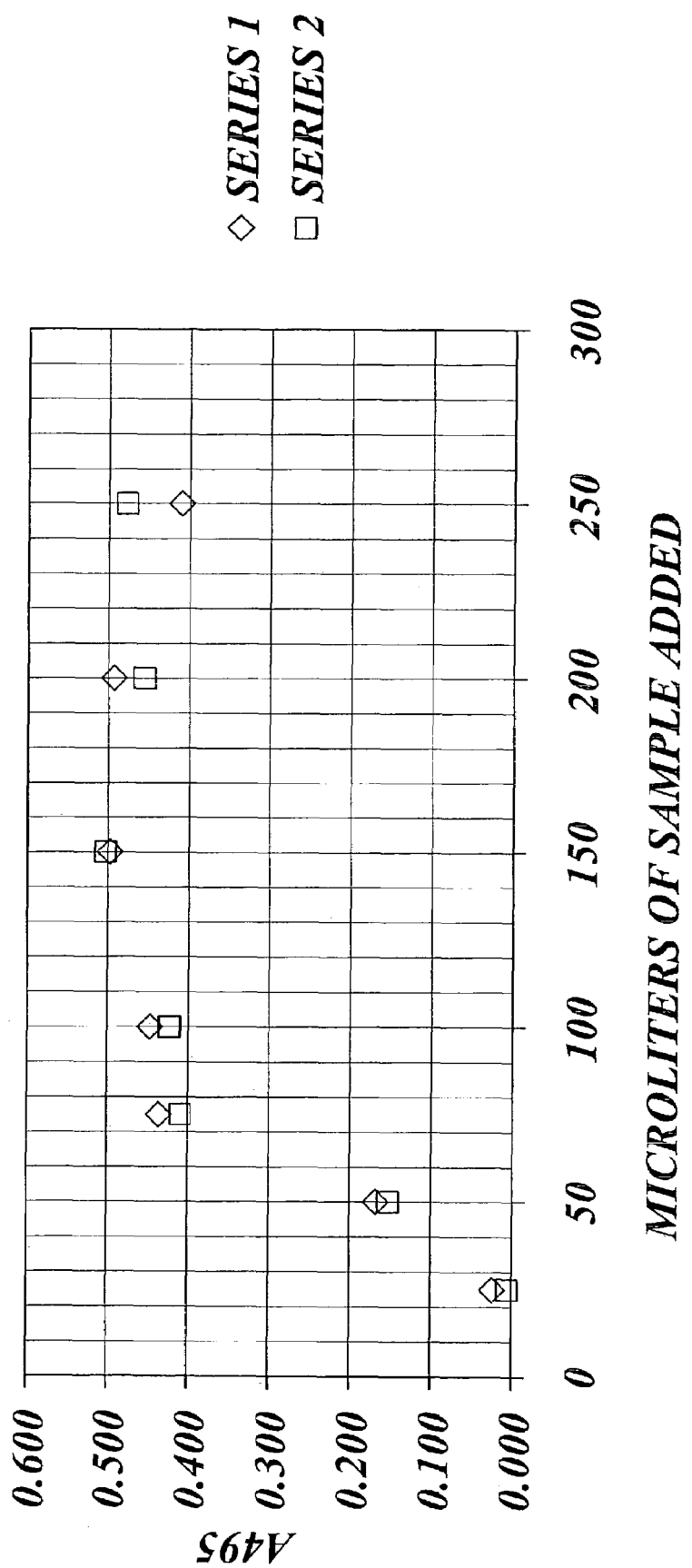
FIG. 13 is a graph illustrating the effect on sample volume added to receiving well on the amount of sample obtained for analysis by a representative method and device of the invention.

FIG. 13 presents the results of an experiment to examine the effect of volume of sample added to the receiving well of the device. As in Example 2, CytoSep 1661 membrane was used and dilutions were produced with 450 microliters of PBSAA diluent. Each dilution was produced 2 minutes after adding the sample to the receiving well. Each volume was tested in duplicate and the volumes tested were 25, 50, 75, 100, 150, 200 and 250 microliters, corresponding to approximately ½, 1, 1½, 2, 3, 4 and 5 drops.

The results indicate that it is necessary to have enough volume to saturate the void volumes of the membrane. Twenty-five and fifty microliter amounts, corresponding to ½ and 1 drop, were insufficient to saturate the CytoSep 1661 sampling membrane, resulting in low A495 readings of 0.168 and below (FIG. 13). However, volumes of 75 microliters and larger, corresponding to 1½ to 5 drops, all saturated the sampling membrane. The samples obtained by the device with these saturating volumes were essentially equivalent based upon their A495 absorbances.

EXAMPLE 5

Effect of Time Delay Between Adding Sample and Adding Diluent on Dilution

Figure 14:
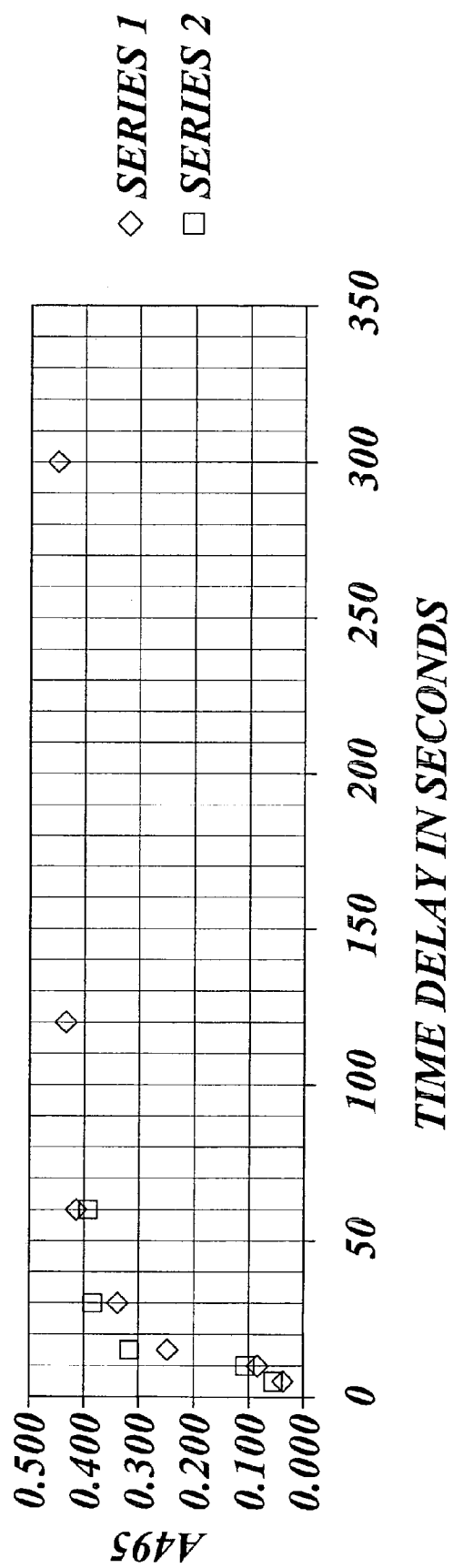
FIG. 14 is a graph illustrating the effect of time delay between adding sample and adding diluent on the final amount of sample obtained for analysis by a representative method and device of the invention.

FIG. 14 presents the results of an experiment to examine the effect of time between sample addition and dilution on the final dilution produced by the method and design of this invention. The experiment was conducted with CytoSep 1661 membrane as in Example 1 using 100 microliters of stock red dye solution. Time periods were tested in duplicate and were 5 seconds, 10 seconds, 15 seconds, 30 seconds and 1 minute. In addition, single dilutions were made after two minutes (120 seconds), five minutes (300 seconds) and fifteen minutes (900 seconds). The results through five minutes are graphed on the figure. At least one full minute was required for the sample to migrate from receiving well end to the area beneath the dilution port and reach a steady state filling the void volume of the membrane at its end opposite the point of application. However, the absorbance at 495 nanometers (A495) remained essentially unchanged from 2 minutes to 15 minutes after adding the sample to the receiving well.

EXAMPLE 6

Preparation of Test Strips for Detecting Antibodies to HIV within Diluted Serum Samples Each test strip was prepared as four separate components. These components include a wick, a micro-particle pad, a white nitrocellulose membrane, and a blotter. The wick serves to draw the diluted sample up into the test strip from the reservoir in the base. The micro-particle pad for these experiments was coated with recombinant protein A (rPA) labeled with colloidal gold, a visually observable micro-particle reagent. As the diluted serum sample migrates through the test strip most of the antibodies within the sample are labeled with the micro-particle reagent and their subsequent migration over the test strip may be tracked. HIV antigen was coated to the nitrocellulose membrane in a line perpendicular to the migration flow. Micro-particle labeled antibodies migrate down the test strip. Those directed at HIV antigen bind to it on the white nitrocellulose, and the remaining labeled antibodies continue migration out of the nitrocellulose into the blotter. The presence of a pink to purple line in the same location as the bound HIV antigen on the nitrocellulose identifies the presence of antibodies directed at that HIV antigen within the diluted serum sample. The blotter paper serves to absorb most of the liquid and reagents that migrate along the test strip, providing a white nitrocellulose background and facilitating recognition of any labeled antibodies bound to the HIV antigen on the white nitrocellulose.

LoProSorb™ from PALL Corporation, Port Washington, N.Y., was used for both the wick and micro-particle application pad. Immunopore™ nitrocellulose paper from Costar Scientific Corporation, Cambridge, Mass., was used for the reading zone of the test, and paper 939 from Ahlstrom Filtration Inc., Chattanooga, Tenn., was used as the blotter.

The micro-particle pad component of the test strips was prepared separately prior to assembly into the final test strips. The micro-particle pad was coated with a solution of colloidal gold-labeled recombinant protein A. The recombinant protein A (rPA), lot RC1041, was obtained from Repligen Corporation, Cambridge, Mass. The colloidal gold-rPA conjugate was prepared as described by Lea et al., J. Histochemistry & Cytochemistry, 40(6):757-758 (1992), with the following modifications. Gold chloride (tetrachlorauric acid trihydrate, ACS, Sigma Chemical Company, St. Louis, Mo.) was dissolved in HPLC pure water at 100 mg gold chloride per liter of HPLC pure water. One hundred ml of this 0.1 mg/ml gold solution was brought to a boil in a Pyrex flask with stirring and precautions to prevent evaporation. A volume of 3.2 ml of 1% sodium citrate was added to the boiling gold solution and stirring continued. The solution initially turned blue-gray, and then with continued stirring and heat the solution became orange-red after two minutes. Heat and stirring were continued another 6 minutes and the solution was then cooled.

The final colloid had an absorbance at 520 nm wavelength of 1.072. A minimal protective test against NaCl was performed with the Lot RC 1041 rPA, and found to be 5 micrograms of rPA per ml of gold colloid. A 40 ml volume of the gold colloid was adjusted to pH 6.0 with $K_2CO_3$ and $H_3PO_4$. Two hundred microliters of rPA at a 1 mg/ml concentration were added with mixing to the pH-adjusted gold colloid solution. The solution was mixed for two minutes and then let stand for four minutes. Two ml of 1% PEG (polyethylene glycol) and 4.6 ml of 10% bovine serum albumin (BSA) were then added with mixing. Twelve aliquots of 1.4 ml each were centrifuged in a Microfuge™ (Beckman Instruments, Fullerton, Calif.), and the solution was centrifuged at maximum speed for 45 minutes. The supernatant above each pellet of gold colloid-rPA was aspirated, and each pellet was resuspended in 50 microliters of a buffer of 50 mM Tris pH 8.0, 100 mM NaCl, 0.02% sodium azide, 0.02% PEG and 1% BSA. All resuspended pellets were pooled and had an absorbance at 520 nanometers of 3.15. This preparation was tested for detection of human IgG coated to nitrocellulose membrane in a lateral flow assay (see below) and showed easily visible strong staining of the IgG that had been coated to the nitrocellulose at concentrations of 1 mg/ml and 10 mg/ml.

The stock colloidal gold rPA conjugate with an absorbance of 3.15 was tested for its ability to bind to antibodies directed at HIV antigens, while preserving the capacity of those antibodies to recognize the HIV antigens. A synthetic peptide representing an immunodominant region of gp41 of HIV-1 was conjugated through its C-terminus to bovine serum albumin as described in Formoso et al. (U.S. Pat. No. 5,260,189). This peptide-protein conjugate was coated to nitrocellulose membrane strips in a line perpendicular to the length of the strip, approximately one-fourth the distance from the downstream terminal end of the strip, at a concentration of 1 mg/ml, and the strips' excess binding sites were then blocked, as described below. Serum containing antibodies to HIV was diluted 1:100 in a buffer consisting of 50 mM Tris HCl, pH 8, 100 mM NaCl, 0.025% sodium azide and 1% BSA. Ten microliters of HIV positive diluted serum was mixed with ten microliters of the stock colloidal gold rPA conjugate, and the colloidal gold rPA conjugate bound to antibodies in test serum. This 20 microliter combination was added to the upstream end of the nitrocellulose strip and allowed to migrate along the nitrocellulose strip past the area of bound HIV peptide-protein conjugate, and off the downstream end of the strip onto a blotter. Most of the visible colloidal gold rPA conjugate migrated through the nitrocellulose paper and onto the blotter, but a reddish-pink line, against a white background, remained at the site on the nitrocellulose where the HIV peptide-protein conjugate had previously been bound. This experiment was repeated using 1:100 diluted serum known to not contain antibodies to HIV, and no visible line remained on the nitrocellulose membrane where HIV peptide-protein conjugate had previously been bound. Taken together, these experiments indicated that the stock colloidal gold rPA conjugate was capable of labeling antibodies to HIV, which then retained their ability to recognize the HIV peptide-protein conjugate bound to the nitrocellulose membrane.

The stock colloidal gold rPA solution was used to prepare microparticle pads for test strips as follows. LoProSorb™ membranes from PALL Corporation, Port Washington, N.Y., that had been backed with polyester (ARCARE 7815, Adhesives Research Inc., Glen Rock, Pa.) were precoated with a solution of nonfat skim milk. The nonfat skim milk blocking buffer consisted of 0.5% nonfat skim milk (Carnation) in deionized water with 50 mM Tris, pH 7.7, 0.03% sodium azide, and 0.45% PVP-40 that had been filter sterilized. After saturating the LoProSorb™ membranes with the blocking solution, they were fully dried and then coated with the stock colloidal gold rPA solution diluted 1:6 in deionized water containing 1% PVP-40, 0.02% sodium azide, 0.1% PEG, 1% BSA, 2.5% sucrose.

These pads containing the colloidal gold microparticles were allowed to air dry prior to assembly into the final test strips.

The HIV antigen coated nitrocellulose membrane component of the test strips was prepared separately prior to assembly into the final test strips. The HIV antigen utilized was peptide 5S76 described by Formoso et al., U.S. Pat. No. 5,260,189. This peptide was conjugated through its C-terminus to bovine serum albumin, and the peptide-protein conjugate was coated to the nitrocellulose. The nitrocellulose membranes employed were Immunopore™ from Corning Costar, Cambridge, Mass., or 5 micron backed nitrocellulose from Schleicher & Schuell (Keene, N.H.). The HIV synthetic peptide-protein conjugate was used in concentrations ranging from 2.5 to 12.5 mg/ml in coating buffer consisting of 50 mM phosphate, 100 mM NaCl, 0.02% sodium azide and 0.05% PVP-40. The HIV peptide-protein conjugate solution was applied to the nitrocellulose in a line perpendicular to the migratory flow of the test strip, and allowed to bind at room temperature for ten minutes. As a control, recombinant protein A in a concentrations ranging from 0.2 mg/ml to 5 mg/ml in the same coating buffer was coated to the same nitrocellulose in a line paralleling the HIV peptide-protein conjugate antigen, separated by 1 cm distance. This was allowed to bind to the nitrocellulose under the same conditions as HIV antigen binding. Remaining active sites on the nitrocellulose were then blocked by gentle rocking of the nitrocellulose immersed in a filter-sterilized solution of blocking buffer consisting of 0.5% nonfat skim milk, 0.45% PV P-40, 0.03% sodium azide in 50 mM Tris, pH 7.7 at room temperature for one hour, followed by air drying.

The final composite test strips were formed by lamination together using single-sided adhesive coated polyester from Adhesives Research Inc., Glen Rock, Pa. (ARCARE 7815 or ARCARE 8160). The first two components to be laminated to the polyester were the antigen coated and blocked nitrocellulose membrane and the wick. The space between wick and nitrocellulose was adjusted so that the subsequent lamination of micro-particle pad coated with colloidal gold labeled rPA produced an overlap region of 2 mm shared on the upstream side with the wick, and on the downstream side with the nitrocellulose membrane. This overlap region allowed capillary flow from one membrane to the other during migration of liquid along the test strip. Subsequently, the blotter paper was laminated to the composite on the downstream side of the nitrocellulose with a 2 mm area of overlap between the blotter and nitrocellulose. The width of the role of laminated four part composite was cut to fit the length dimension of the test strip channel of the medical device (FIGS. 6, 6-5). Prior to use, a single test strip was cut from the composite with a width to fit the width of the test strip channel of the medical device.

EXAMPLE 7

Detection of Antibodies to HIV Using Test Strips

Serum known to contain antibodies to HIV was compared to serum that did not contain antibodies to HIV, in dilutions ranging from 1:10 through 1:4000, using the test strips of Example 6. The serum samples were diluted in a PBSAA diluent described in Example 1. With the samples known to contain antibodies to HIV, a visible line of colored microparticles appeared on the test strips in the location of bound HIV antigen, in serum dilutions of 1:10 through 1:2,000. This indicated sensitive detection of antibodies to HIV in the known positive samples. No such visible line of microparticles developed for the samples that did not contain antibodies to HIV. This indicated specificity of the test strips configured as in Example 6. The control line of nitrocellulose bound rPA produced a visible line of micro-particles at serum dilutions of 1:10 through 1:300, independent of the presence of antibodies to HIV. This indicates that rPA coated to the nitrocellulose membrane under the conditions of Example 6 can be adapted for use as a control to confirm that an adequate amount of serum immunoglobulin was evaluated to validate a negative test result. This use of rPA as a control to confirm adequate serum added is illustrated in FIG. 10, well C3, regarding interpretation of test results.

EXAMPLE 8

Use of Device and Method to Detect Antibodies to HIV to Free gp41 HIV-1 Peptide Coated to Test Strips.

Peptide PVIR 126, an antigenic peptide from gp41 of HIV-1, was obtained from Bachem California (Torrance, Calif.). Peptide PVIR has the amino acid sequence H$_2$N-Arg-Ile-Leu-Ala-Val-Glu-Arg-Tyr-Leu-Lys-Asp-Gln-Gln-Leu-Leu-Gly-Ile -Trp-Gly-Cys-Ser-Gly-Lys-Leu-Ile-Cys-Thr-Thr-Ala-Val-Pro-Trp-Asn-Ala-Ser-OH (SEQ ID NO:1) with some cyclization of the peptide by an S-S creating an antigenic loop in the underlined portion. This peptide was dissolved in 1% acetic acid at 2 mg/ml, and then diluted to 0.5 mg/ml using a nitrocellulose coating buffer consisting of 50 mM phosphate pH 7.4, 150 mM NaCl, 0.05% PVP-40, and 0.025% sodium azide. The peptide in nitrocellulose coating buffer was applied to nitrocellulose strips taken from the nitrocellulose contained within the Schleicher & Schuell (Keene, N.H.) AccuSep™ membrane as 3 drops of 1.5 microliters each in a line and allowed to air dry. Upstream from the nitrocellulose on each strip was first a microparticle application pad connecting to the nitrocellulose by at least 3 mm and further upstream a wick connected to the micro-particle pad by at least 3 mm. Downstream from the nitrocellulose was a blotter that connected to the nitrocellulose by at least 3 mm of overlap. The wick was comprised of LoProSorb membrane from Pall-Gelman (Port Washington, N.Y.). The microparticle pad was prepared by pretreating the LoProSorb membrane with 0.1% IgG free BSA and drying, followed by application of protein A colloidal gold (20 nm size, 8 O.D. in 5% trehalose) obtained from British Biocell International, Cardiff, UK. The colloidal gold was added to pad saturation and allowed to dry, and the pads used with each strip were approximately 5 mm wide by 10 mm long. The blotter was comprised of S&S paper 300 and served to wick all fluid moving along the test strip from the wick, through the microparticle/colloidal gold pad and onto the nitrocellulose strip coated with PVIR gp41 peptide and out the downstream end of the test strip into the S&S 300 paper blotter.

The test strips were first tested with a 1:100 dilution of a pool of 9 HIV positive sera, and compared with a 1:100 dilution of an HIV negative test serum. The colloidal gold particles with attached HIV antibodies bound to the test strip in the area of applied peptide for the HIV positive serum sample, but not for the HIV negative serum sample.

The test strips were then placed into the test device of this patent application. Whole blood negative for HIV antibody was then used as the negative control, and compared to this same blood mixed two parts whole blood to 1 part HIV positive serum pool. The test device was run in the normal fashion with separation of the red blood cells from serum over CytoSep 1661 (Pall-Gelman), followed by creation of a dilution of approximately 1:90 through the sampling port by the addition of serum dilution buffer consisting of 50 mM phosphate, 150 mM NaCl, 0.1% BSA (IgG free) and 0.025% sodium azide. The prepared and diluted whole blood samples wicked up onto the test strips from the sampling port well, and ran along the test strips through the microparticle pads picking up the colloidal gold protein A, and migrating along the nitrocellulose membranes past the bound PVIR gp41 peptide and into the blotter. The HIV positive whole blood-serum mixture caused the colloidal gold to bind to the peptide region of the nitrocellulose membrane strips, and this binding did not occur with the HIV negative whole blood.

EXAMPLE 9

Use of Device and Method to Detect Antibodies to H. pylori Antigen Coated to Test Strips Test strips were prepared identically to those in Example 8 except that the nitrocellulose membrane used were test strips from the Beckman-Coulter (Palo Alto, Calif.) Flex-Sure HPTM tests that contain an H. pylori antigen line. These test strips were placed into the test device of this patent and reacted against whole blood from a person with antibody to H. pylori and another person without antibody to H. pylori, as in Example 9. The prepared and diluted whole blood samples wicked onto the test strips within the device and the sample with antibodies to H. pylori caused the colloidal gold particles to collect at the H. pylori antigen line, whereas the sample without H. pylori antibodies was unable to cause the colloidal gold to collect at the H. pylori line on the test strips.

EXAMPLE 10

Use of Device and Method to Detect HCG Antigen in Whole Blood

Dipsticks used to detect human chorionic gonadotrophin (HCG) in urine or serum were obtained from Vancouver Biotech Ltd., Vancouver, British Columbia, Canada. These strips were placed into the test device of this patent and run and tested against three whole blood samples. One sample was from a pregnant female, and two samples were from males whose blood did not contain HCG. Sixty-six microliters of whole blood was placed into the blood collection well of the device, and allowed to migrate along the CytoSep 1661 membrane within it separating red blood cells from serum, over a three minute period. After three minutes, the sampling port was depressed and locked into place and 250 microliters of serum dilution buffer consisting of 50 mM phosphate, pH 7.4, 150 mM NaCl, 0.025% sodium azide, and 0.1% BSA (IgG free) was added through the port to collect and dilute the serum samples from each person. These prepared and diluted samples then wicked over the dipstick test strips from Vancouver Biotech Ltd. All three strips showed the control line, but only the pregnant female showed a line in the area where monoclonal antibody to HCG had been coated.

While the preferred embodiment of the invention has been illustrated and described, it will be appreciated that various changes can be made therein without departing from the spirit and scope of the invention.

---

The invention claimed is:

1. A method for sampling a fluid, comprising:
   (a) saturating at least a portion of a compressible porous membrane with a first fluid, wherein the first fluid is applied to the membrane at a position other than a portion of the membrane to be isolated and is migrated to saturate the portion of the membrane to be isolated;
   (b) isolating the portion of the membrane to be isolated by applying compressive force on top and bottom surfaces of the membrane along the perimeter of the area to be isolated thereby defining a non-compressed area of saturated membrane centripetal to the compressed perimeter; and
   (c) delivering a second fluid under pressure to the isolated portion of the membrane to release the first fluid from the isolated portion of the membrane.

2. The method of claim 1, wherein the isolated portion of the membrane defines a predetermined volume sample of the first fluid.

3. The method of claim 1, wherein the first fluid comprises a biological fluid.

4. The method of claim 1, wherein the first fluid comprises whole blood and the isolated portion of the membrane comprises its serum or plasma components.

5. The method of claim 1, wherein the migration of the first fluid along the membrane separates components in the first fluid.

6. The method of claim 1, wherein the membrane has a substantially uniform porous structure.

7. The method of claim 1, wherein the second fluid comprises a gas.

8. The method of claim 1, wherein the second fluid comprises a liquid.

9. The method of claim 1, wherein the second fluid is applied in a specified quantity.

10. The method of claim 9, wherein the second fluid comprises a liquid.

11. A method for diluting a liquid sample, comprising:
    (a) saturating at least a portion of a compressible porous membrane with a liquid, wherein the liquid is applied to the membrane at a position other than a portion of the membrane to be isolated and is migrated to saturate the portion of the membrane to be isolated;
    (b) isolating the portion of the membrane to be isolated by applying compressive force on top arid bottom surfaces of the membrane along the perimeter of the area to be isolated thereby defining a non-compressed area of saturated membrane centripetal to the compressed perimeter; and
    (c) delivering a diluent under pressure to the isolated portion of the membrane to release the liquid sample from the isolated portion of the membrane to provide a diluted liquid sample.

12. The method of claim 11, wherein the isolated portion of the membrane defines a predetermined volume of the liquid sample.

13. The method of claim 11, wherein the liquid sample comprises a biological fluid.

14. The method of claim 11, wherein the liquid sample comprises whole blood and the isolated portion of the membrane comprises its serum or plasma components.

15. The method of claim 11, wherein the migration of the liquid along the membrane separates components in the liquid.

16. The method of claim 11, wherein the membrane has a substantially uniform porous structure.

17. The method of claim 11, wherein the diluent is applied in a specified quantity.

18. A method for detecting an analyte in a liquid sample, comprising:
    (a) saturating at least a portion of a compressible porous sample receiving membrane with a liquid containing an analyte, wherein the liquid is applied to the membrane at a position other than a portion of the membrane to be isolated and is migrated to saturate the portion of the membrane to be isolated;
    (b) isolating the portion of the membrane to be isolated by applying compressive force on top and bottom surfaces of the membrane along the perimeter of the area to be isolated thereby defining a non-compressed area of saturated membrane centripetal to the compressed perimeter, wherein a sample of the liquid is isolated; and
    (c) delivering a diluent under pressure to the isolated portion of the membrane to release the liquid sample from the isolated portion of the membrane to provide a diluted liquid sample; and
    (d) directing the diluted liquid sample to one or more test strips that are distinct from the sample receiving membrane, wherein the presence of the analyte may be detected.

19. The method of claim 18, wherein the isolated portion of the membrane defines a predetermined volume of the liquid sample.

20. The method of claim 18, wherein the liquid sample comprises a biological fluid.

21. The method of claim 18, wherein the liquid comprises whole blood and the isolated portion of the membrane comprises its serum or plasma components.

22. The method of claim 18, wherein the migration of the liquid along the membrane separates components in the liquid.

23. The method of claim 18, wherein the diluent is applied in a specified quantity.

24. The method of claim 18, wherein the diluted liquid sample is directed to a receptacle in fluid communication with the test strip.

25. The method of claim 18, wherein the diluted liquid sample is directed to a receptacle in fluid communication with one or more test strips and a control strip.

26. The method of claim 18, wherein the analyte comprises an HIV antibody.

27. The method of claim 18, wherein the analyte comprises an antibody to *H. pylori* antigen.

28. The method of claim 18, wherein the analyte comprises HCG antigen.

* * * * *

UNITED STATES PATENT AND TRADEMARK OFFICE
CERTIFICATE OF CORRECTION

PATENT NO. : 7,364,914 B2  Page 1 of 1
APPLICATION NO. : 10/413446
DATED : April 29, 2008
INVENTOR(S) : Thomas M. Buchanan It is certified that error appears in the above-identified patent and that said Letters Patent is hereby corrected as shown below:

| COLUMN | LINE | ERROR |
| --- | --- | --- |
| Title Page item [73] | Assignee | "Summer" should read --Sumner-- |
| 23 | 45 | "arid" should read --and-- |
| 23 | 59 | after "wherein the liquid" delete "sample" |

Signed and Sealed this

Sixth Day of January, 2009

JON W. DUDAS
*Director of the United States Patent and Trademark Office*